United States Patent
Jermy et al.

(10) Patent No.: US 11,793,892 B2
(45) Date of Patent: *Oct. 24, 2023

(54) NANOSILICA CARRIER WITH SPIONS AND A CURCUMINOID

(71) Applicant: Imam Abdulrahman Bin Faisal University, Dammam (SA)

(72) Inventors: B. Rabindran Jermy, Dammam (SA); Vijaya Ravinayagam, Dammam (SA)

(73) Assignee: Imam Abdulrahman Bin Faisal University, Dammam (SA)

(*) Notice: Subject to any disclaimer, the term of this patent is extended or adjusted under 35 U.S.C. 154(b) by 226 days.

This patent is subject to a terminal disclaimer.

(21) Appl. No.: 17/348,911

(22) Filed: Jun. 16, 2021

(65) Prior Publication Data

US 2021/0322580 A1 Oct. 21, 2021

Related U.S. Application Data

(62) Division of application No. 16/055,221, filed on Aug. 6, 2018, now Pat. No. 11,471,542.

(51) Int. Cl.
*A61K 9/00* (2006.01)
*A61K 49/04* (2006.01)
(Continued)

(52) U.S. Cl.
CPC .......... *A61K 49/0428* (2013.01); *A61K 31/12* (2013.01); *A61K 47/6803* (2017.08);
(Continued)

(58) Field of Classification Search
CPC .................................................... A61K 31/12
See application file for complete search history.

(56) References Cited

U.S. PATENT DOCUMENTS

| | | | |
|---|---|---|---|
| 9,220,685 | B2 | 12/2015 | Trogler et al. |
| 2010/0255103 | A1 | 10/2010 | Liong et al. |
| 2011/0268970 | A1 | 11/2011 | Ying et al. |

FOREIGN PATENT DOCUMENTS

| | | |
|---|---|---|
| CN | 103551094 B | 4/2015 |
| CN | 105084424 A | 11/2015 |

(Continued)

OTHER PUBLICATIONS

Huang, Novel drug delivery nanosystems based on out-inside bifunctionalized mesoporous silica yold-shell magnetic nanostars used as nanocarriers for curcumin, Journal of Materials Chemistry B, 4(1), 46-56 (Year: 2016).*

(Continued)

*Primary Examiner* — Paul W Dickinson
(74) *Attorney, Agent, or Firm* — Oblon, McClelland, Maier & Neustadt, L.L.P.

(57) ABSTRACT

Silica nanocarriers hybridized with superparamagnetic iron oxide nanoparticles ("SPIONs") and curcumin through equilibrium or enforced adsorption technique. Methods for dual delivery of SPIONs and curcumin to a target for diagnosis or therapy, for example, for SPION-based magnetic resonance imaging or for targeted delivery of curcumin to a cell or tissue. The technique can be extend to co-precipitation of mixed metal oxide involving Ni, Mn, Co and Cu oxide. The calcination temperature can be varied from 500-900° C. The nanocombination is functionalized with chitosan, polyacrylic acid, PLGA or another agent to increase its biocompatibility in vivo.

13 Claims, 14 Drawing Sheets

(51) Int. Cl.
  *A61K 49/18* (2006.01)
  *A61K 49/08* (2006.01)
  *A61K 47/68* (2017.01)
  *A61K 47/69* (2017.01)
  *A61K 31/12* (2006.01)
  *A61P 35/00* (2006.01)
  *B82Y 5/00* (2011.01)

(52) U.S. Cl.
  CPC ...... *A61K 47/6883* (2017.08); *A61K 47/6923* (2017.08); *A61K 47/6929* (2017.08); *A61K 49/08* (2013.01); *A61K 49/1878* (2013.01); *A61P 35/00* (2018.01); *B82Y 5/00* (2013.01)

(56) References Cited

FOREIGN PATENT DOCUMENTS

| CN | 104740653 B | 9/2017 |
|---|---|---|
| IN | 880/CHE/2011 | 6/2013 |
| WO | 2008/048074 A1 | 4/2008 |
| WO | 2017/041032 A1 | 3/2017 |
| WO | 2017/041033 A1 | 3/2017 |

OTHER PUBLICATIONS

Wahajuddin, et al.; Superparamegnetic iron oxide nanoparticles: magnetic nanoplatforms as drug carries; International Journal of Nonomedicine; Jul. 5, 2012; 27 Pages.

Zhu, et al.; Controlled synthesis of core/shell magnetic iron oxide/ carbon systems via a self-template method; Journal of Materials Chemistry, 19 (41), 7710-7715; 2009; 7 pages.

Huang, et al.; Novel drug delivery nanosystems based on out-inside bitfunctionalized mesoporous silica yolk-shell magnetic nanostars used as nanocarriers for curcumin; Journal of Materials Chemistry B, Issue 1, 2016; 7 pages.

Yu, et al.; Preparation of magnetic mesoporous silica nanoparticles as a ultifunctional platform for potential drug delivery and hyperthermia; Science and technology ofAdvanced Materials, vol. 17, No. 229-238; 2016; 10 pAges.

Lu, et al.; Iron oxide-loaded hollow mesoporous silica nanocapsules for controlled drug release and hyperthermia; Chemical Communications, Issue 97; 2013; Dec. 1, 2017; Abstract; 1 Page.

Sivakumar, et al.; Highly versatile SPION encapsulated PLGA nanoparticles as photothermal ablators of cancer cells and as multimodal imaging agents; Biomaterials Science, Issue 3; 2017; Abstract; 2 pages.

Studying the loading effect of acidic type antioxidant on amorphous silica nanoparticles carriers; Journal of Nanoparticle Research; Jun. 2017; Abstract; 8 Pages.

* cited by examiner

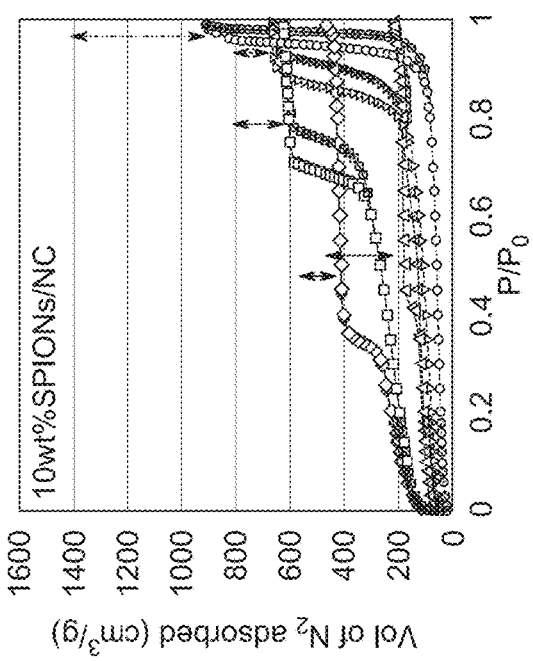
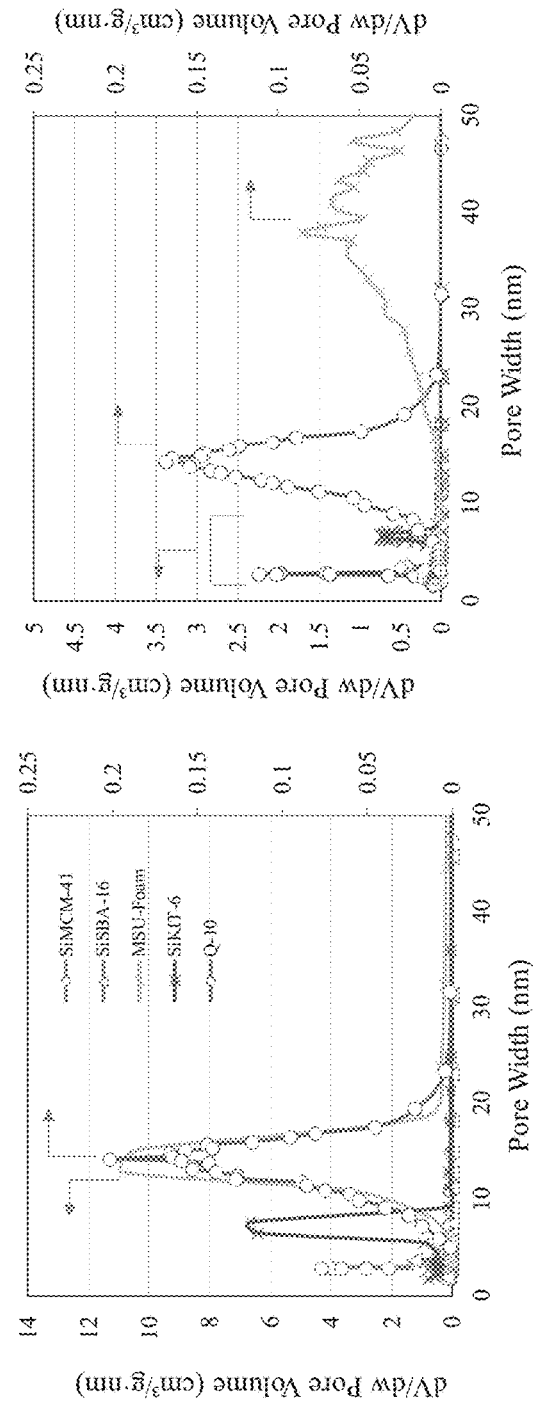
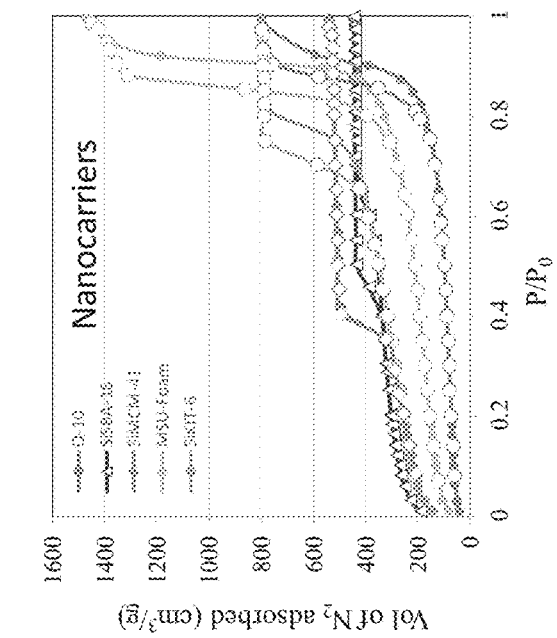
FIG. 2A  FIG. 2B  FIG. 2C  FIG. 2D

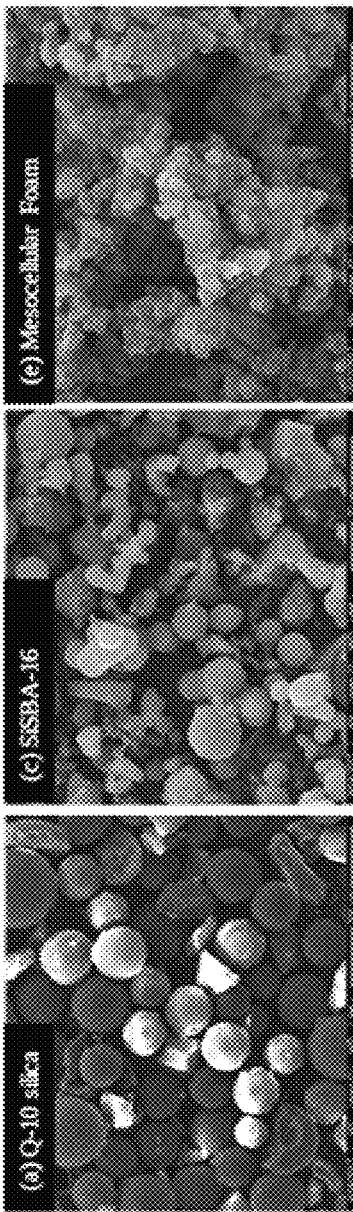
FIG. 6A FIG. 6B FIG. 6C FIG. 6D FIG. 6E FIG. 6F

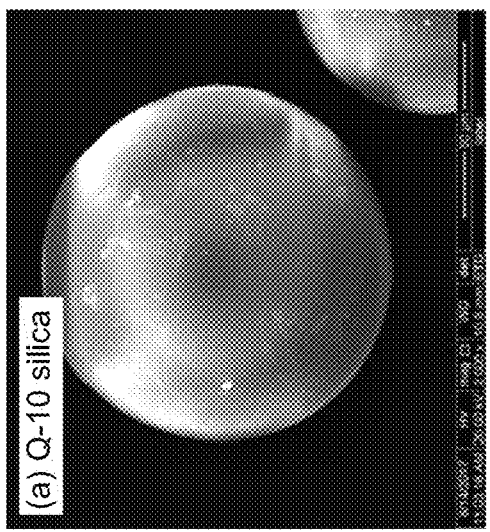
FIG. 7A (a) Q-10 silica
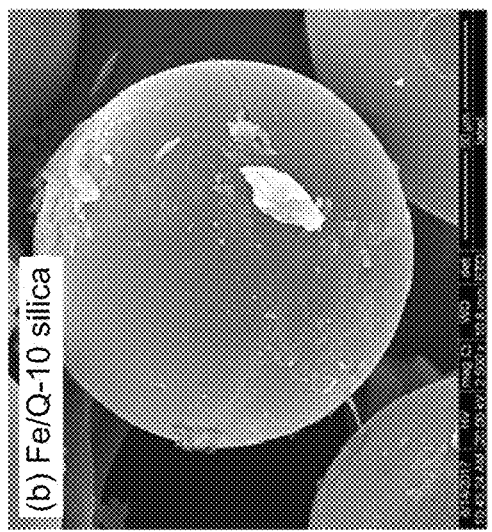
FIG. 7B (b) Fe/Q-10 silica
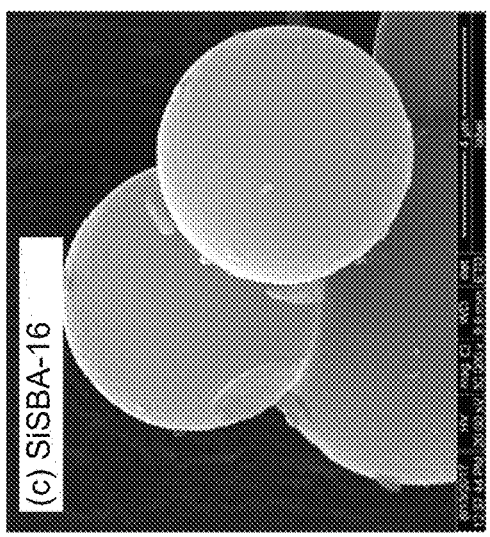
FIG. 7C (c) SiSBA-16
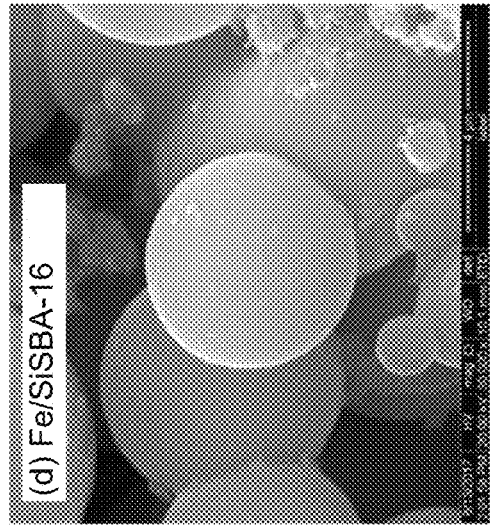
FIG. 7D (d) Fe/SiSBA-16
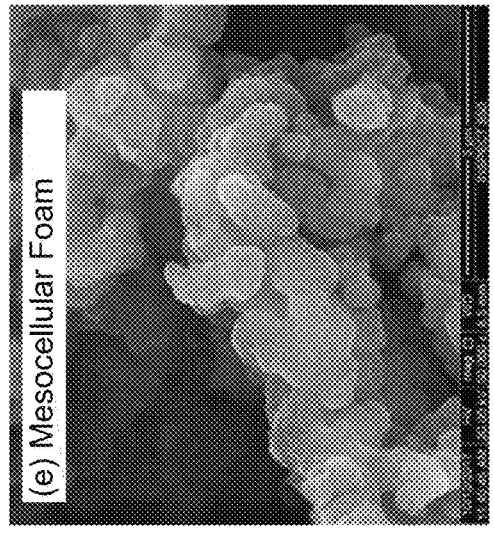
FIG. 7E (e) Mesocellular Foam
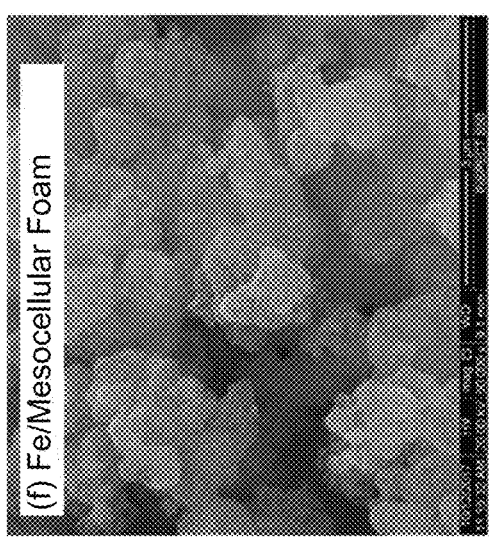
FIG. 7F (f) Fe/Mesocellular Foam FIG. 9
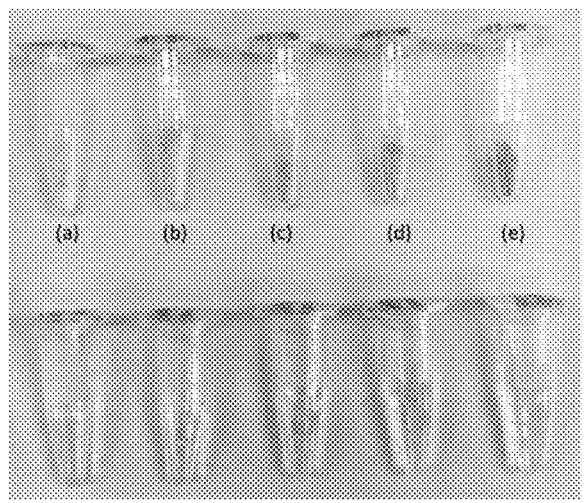
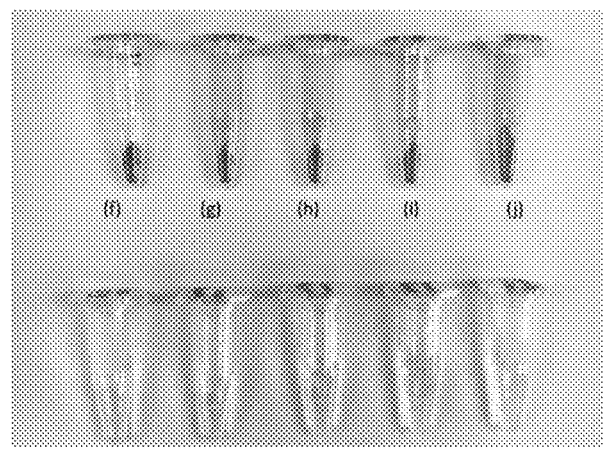

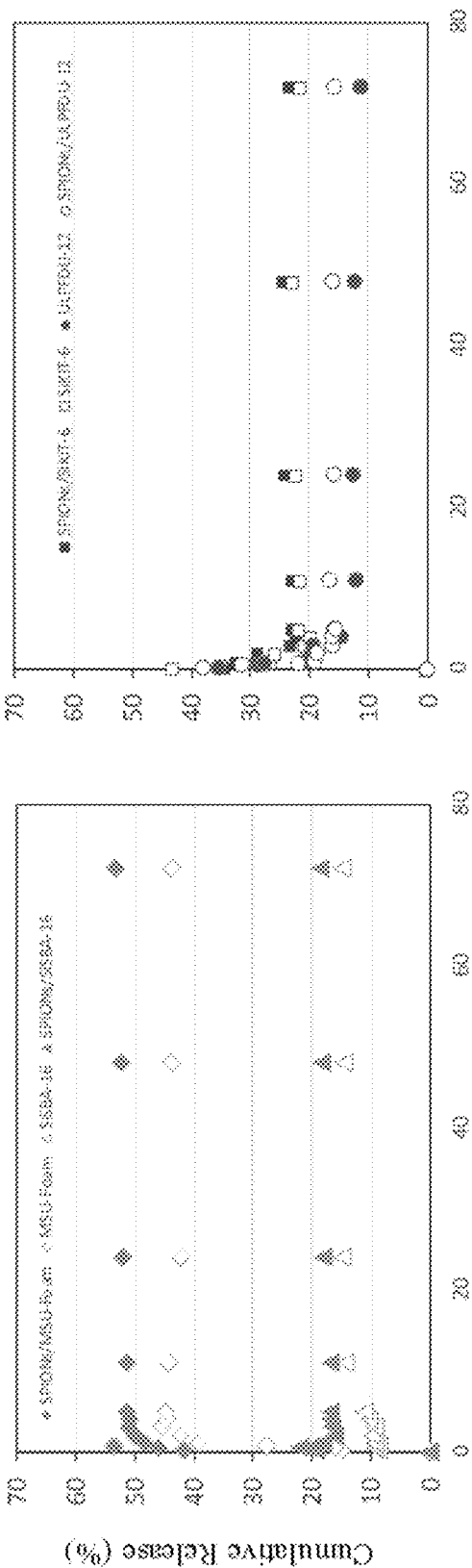

FIG. 12A
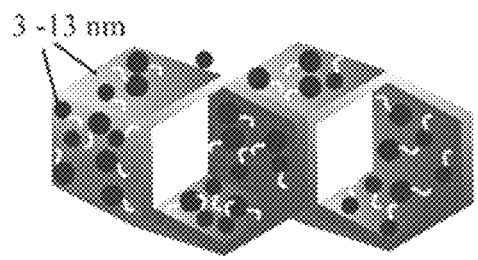
Magnetically inactive SPIONs/SiMCM-41
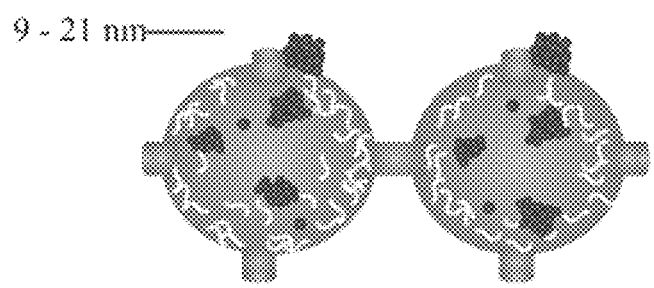
Magnetically active SPIONs/SiSBA-16
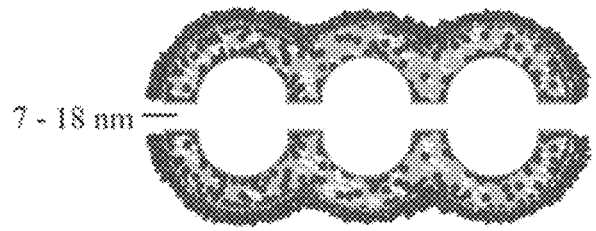
Magnetically active SPIONs/Mesocellular foam)

Magnetically active nanoparticles

NANOSILICA CARRIER WITH SPIONS AND A CURCUMINOID

CROSS-REFERENCE TO RELATED APPLICATIONS

The present application is a Divisional of U.S. application Ser. No. 16/055,221, having a filing date of Aug. 6, 2018.

BACKGROUND OF THE INVENTION

Field of the Invention

The embodiments herein generally relate to the field of nanomedicine, molecular imaging, and drug delivery.

Description of Related Art

The "background" description provided herein is for the purpose of generally presenting the context of the disclosure. Work of the presently named inventor(s), to the extent it is described in this background section, as well as aspects of the description which may not otherwise qualify as prior art at the time of filing, are neither expressly or impliedly admitted as prior art against the present invention.

Cancer Treatment Limitations. The scope of therapeutic approaches to treatment of deadly diseases such as cancer and diabetes as well as other metabolic disorders has been expanded and redefined by recent interdisciplinary research between medicine and nanotechnology (nanomedicine). In particular, the treatment of cancer poses major challenges worldwide. Numbers of cancer-related deaths, morbidities, and incidence are all rising; there are over 6 million cancer related deaths worldwide. Cancer incidence is expected to continue to rise and the number of people with cancer is expected to rise to about 24 million by 2035.

Cancer treatments, such as conventional surgery as well as chemo-, radio- and photodynamic-therapies, are insufficient to address these challenges. Further, an anticancer therapy for one type of cancer may be ineffective for treatment of another type of cancer, for example, an anticancer therapy for skin cancer may be incompetent for treating breast, liver, lung, or colon cancer.

Conventional cancer treatments suffer from many other limitations. While surgery is often an effective way to treat solid, non-metastatic cancers, additional therapy is frequently needed if residual or metastatic cancer cells remain after surgery. Radiotherapy targets high energy radiation to bodily locations containing cancer cells in order to damage and kill the cancer cells. However, in also exposes normal, non-cancerous cells to the radiation and can result in the formation of secondary malignancies. Chemotherapy is relatively non-selective and can damage normal cells and tissues as well as cancer cells. It often causes unacceptable side-effects especially when used over a long period of time.

In view of these limitations of different conventional anti-cancer therapies, there is an imminent need for a way to selectively target cancer cells in the body with less toxic agents that can selectively inhibit the growth of or kill cancer cells.

Curcumin and related curcuminoids may have such a potential if properly targeted to cancer cells in amounts effective to inhibit cancer cell growth. However, curcumin exhibits difficult pharmacokinetic properties, such as poor solubility in aqueous media and poor bioavailability to tissues containing cancer cells. Curcumin in an antioxidant found in nature having a polyphenol structure and may exhibit anti-cancer pharmacodynamic properties. Many antioxidants are known to act against cancers, including against leukemia, colon and lung cancer cells, and against other metabolic disorders through free radical scavenging abilities.

Curcumin is widely used as a traditional medicine. It has been long postulated as an anti-cancer drug due to its antioxidant properties (Kant V, Gopal A, Pathak N N, Kumar P, Tandan S K, Kumar D. Antioxidant and anti-inflammatory potential of curcumin accelerated the cutaneous wound healing in streptozotocin-induced diabetic rats. Int Immunopharmacol. 2014 June; 20(2):322-30. doi: 10.1016/j.intimp.2014.03.009. Epub 2014 Mar. 24. PubMed PMID: 24675438; Ak T, Gülçin I. Antioxidant and radical scavenging properties of curcumin. Chem Biol Interact. 2008 Jul. 10; 174(1):27-37. doi: 10.1016/j.cbi.2008.05.003. Epub 2008 May 7. PubMed PMID: 18547552).

Interestingly, it was also reported to induce reactive oxygen species (ROS) (Gersey Z C, Rodriguez G A, Barbarite E, Sanchez A, Walters W M, Ohaeto K C, Komotar R J, Graham R M. Curcumin decreases malignant characteristics of glioblastoma stem cells via induction of reactive oxygen species. BMC Cancer. 2017 Feb. 4; 17(1):99. doi: 10.1186/s12885-017-3058-2. PubMed PMID: 28160777; PubMed Central PMCID: PMC5292151; Larasati Y A, Yoneda-Kato N, Nakamae I, Yokoyama T, Meiyanto E, Kato J Y. Curcumin targets multiple enzymes involved in the ROS metabolic pathway to suppress tumor cell growth. Sci Rep. 2018 Feb. 1; 8(1):2039. doi: 10.1038/s41598-018-20179-6. PubMed PMID: 29391517; PubMed Central PMCID: PMC5794879).

When ROS are present at low levels, it induces tumor proliferation. However, when the ROS are at extremely high levels, it induces cell death, which is one of the suggested anti-tumor mechanisms of curcumin (Gersey et al, 2017). Curcumin was reported to influence progression into the cell cycle (cyclin D1, p53), and affect anti- and pro-apoptotic pathways (Ravindran J, Prasad S, Aggarwal B B. Curcumin and cancer cells: how many ways can curry kill tumor cells selectively? AAPS J. 2009 Sep.; 11(3):495-510. doi: 10.1208/s12248-009-9128-x. Epub 2009 Jul. 10. Review. PubMed PMID: 19590964; PubMed Central PMCID: PMC2758121; Zeng et al, 2018; and Gersey et al, 2017). In hepatocellular carcinoma cell lines, curcumin treatment resulted in a significant increase in the cyclin-dependent kinase inhibitor 1A (CDKN1A), which subsequently resulted in cell cycle arrest (Zeng Y, Shen Z, Gu W, Wu M. Inhibition of hepatocellular carcinoma tumorigenesis by curcumin may be associated with CDKN1A and CTGF. Gene. 2018 Feb. 2. pii: S0378-1119(18)30104-5. doi: 10.1016/j.gene.2018.01.083. [Epub ahead of print] PubMed PMID: 29408622). Curcumin treated glioblastoma tumor biopsies had lower proliferation and reduced ability to form tumor colonies (Gersey et al, 2017). These reports suggest that curcumin exhibits broad anti-tumor properties.

However, there are a numerous issues hindering the use of curcumin as a therapeutic drug. These issues include: rapid metabolism, poor absorption, poor bioavailability, insolubility in water, and chemical instability. These problems may explain the conflicting results in clinical trials especially in that the administration was through the oral route (Nelson K M, Dahlin J L, Bisson J, Graham J, Pauli G F, Walters M A. *The Essential Medicinal Chemistry of Curcumin*. J Med Chem. 2017 Mar. 9; 60(5):1620-1637. doi: 10.1021/acs.jmedchem.6b00975. Epub 2017 Jan. 11. Review. PubMed PMID: 28074653; PubMed Central PMCID: PMC5346970).

Many forms of nanosilicas are used in non-medical applications including their use in the chemical and electronic fields, for example, as parts of or supports for chemical catalysts, or for use in magnetic, electronic, dielectric, optical, batteries and other related applications. Nanosilicas are currently being investigated for biomedical applications including for drug delivery. For example, a payload molecule may be encapsulated within a nanosilicate carrier to attempt to improve payload biocompatibility, stability and biodegradability; J. T. Cole, N. B. Holland, *Multifunctional nanoparticles for use in theranostic applications*, Drug Deliv. and Transl. Res. 5 (2015) 295-309. A nanosilica carrier may shield a payload molecule from degradation or elimination in body and might function to improve the pharmacokinetic properties of some molecules.

Prior attempts to load and deliver curcuminoids to target cancer tissues have not been able to deliver adequate amounts of curcumin to a target tissue or to follow the distribution of curcumin once administered. These problems spring in part from a lack of a method to provide a deliverable form of curcumin.

Recent research by the inventors has shown that structured silica such as SBA-16 has a great capability to carry acidic type antioxidants such as gallic acid; V. Ravinayagam, B. Rabindran Jermy, *Studying the loading effect of acidic type antioxidant on amorphous silica nanoparticle carriers*, 19 (2017) 190. However, in contrast to gallic acid, antioxidants such as curcumin are difficult to work with and present specific problems. For example, while curcumin encapsulated surfactant complexes, hydrogels, liposomes have been studied methods for their preparation are rather complex, especially for large scale implementation. Moreover, such methods provide products having reduced stability or solubility in biological environments; R. S. Mulik, J. Monkkonen, R. O. Juvonen, K. R. Mahadik, A. R. Paradkar, Int. J. Pharm. 398 (2010) 190-203.

Curcumin encapsulated into MCM-41 type mesoporous silica was shown to improve the solubility, enhance drug release, and result in a higher cellular delivery; S. Jambhrunkar, S. Karmakar, A. Popat, M. Yu, C. Yu, *Mesoporous silica nanoparticles enhance the cytotoxicity of curcumin*, RSC Adv. 4 (2014) 709-712. However, rapid disintegration of curcumin and cytotoxicity towards normal and cancer cell lines were observed; Q. J. He, J. L. Shi, F. Chen, M. Zhu and L. X. Zhang, Biomaterials, 2010, 31, 3335.

Mesotextured silicas such as hexagonal MCM-41, SBA-15 and cubic SBA-16, MCM-18 have been reported to function as drug delivery agents in in vitro and in vivo; I. I. Slowing, J. L. Vivero-Escoto, C. W. Wu, V. S. Lin, *Mesoporous silica nanoparticles as controlled release drug delivery and gene transfection carriers*, Adv Drug Deliv Rev. 60 (2008) 1278-1288; S. Kwon, R. K Singh, R. A. Perez, E. A. About Neel, H-W. Kim, W. Chrzanowski, *Silica based mesoporous nanoparticles for controlled drug delivery*, J Tissue Eng. 2013; 4: 2041731413503357. However, recent studies have shown poor bioavailability of drugs targeted with silica nanocarriers and that so far only 5% of a drug reaches targeted tumors. This is comparable to the amount of a conventional drug, which does not contain a nanocarrier, delivered. Conventional nanocarriers also lack a means to track and measure targeted delivery of drugs such as curcumin to target sites.

Multifunctional theranostic nanoparticles have been used for drug delivery and tumor identification. These represent combinations of therapeutic compounds with tumor imaging agents; M. Howell, C. Wang, A. Mahmoud, G. Hellermann, S. S. Mohapatra, S. Mohapatra, *Dual-function theranostic nanoparticles for drug delivery and medical imaging contrast: perspectives and challenges for use in lung diseases*, Drug Deliv. and Transl. Res. 3(2013)352-363.

Magnetic drug targeting has been proposed. This involves design of a drug or imaging composition that can be magnetically guided to a target. Prior attempts have shown that incorporating a drug and a magnetic agent in a single composition was cumbersome and challenging. Such a composition can suffer from toxicity due to incorporation of toxic levels of magnetic particles or from issues of biocompatibility such as induction of inflammatory responses in respiratory system. However, some FDA approved SPIONs have intrinsic magnetic properties that may have the potential to be used in combination with anticancer drugs. Moreover, SPION-based compositions have the potential to be functionalized on their iron oxide surfaces; J. Estelrich, E. Escribano, J. Queralt, M. A. Busquets, *Iron Oxide Nanoparticles for Magnetically-Guided and Magnetically-Responsive Drug Delivery*, Int J Mol Sci. 16 (2015) 8070-8101. Magnetic $Fe_3O_4$-based mesoporous silica such as SBA-15 (p6 mm), mesocellular foams and fiber type of silica have been previously prepared; S. Huang, C. Li, Z. Cheng, Y. Fan, P. Yang, C. Zhang, K. Yang, J. Lin, *Magnetic $Fe_3O_4$ mesoporous silica composites for drug delivery and bioadsorption*, Journal of Colloid and Interface Science, 376 (2012) 312-321; Carbohydrate Polymers 171 (2017) 259-266.

Magnetic mesoporous silica particles have been used in hyperthermia therapy; Z. Tian, X. Yu, Z. Ruan, M. Zhu, Y. Zhu, N. Hanagata, *Magnetic mesoporous silica nanoparticles coated with thermo-responsive copolymer for potential chemo-and magnetic hyperthermia therapy*, Microporous and Mesoporous Materials 256 (2018) 1-9.

Amine-functionalized iron oxide/SBA-16 nanocomposites have been used as dual imaging tools and were able to carry large protein molecules including antibodies; H. H. P. Yiu, H-j Niu, E. Biermans, G. vanTendeloo, M. J. Rosseinsky, *Designed Multifunctional Nanocomposites for Biomedical Applications* Adv. Functional Mater. 2010, 20, 1-11.

Curcumin loaded in the SPIONs and coated hyaluronic acid (fluorescent dye) has been used for MM as well as fluorescent imaging studies; D. Lachowicz, A. Szpak, K. E. Malek-Zietekc, M. Kepczynski, R. N. Mullerd, S. Laurent, M. Nowakowska, S. Zapotoczny. *Biocompatible and fluorescent superparamagnetic iron oxide nanoparticles with superior magnetic properties coated with charged polysaccharide derivatives*, Colloids and Surfaces B: Biointerfaces 150 (2017) 402-407.

Magnetic nanosilicas have been used as transfecting agents; F. Scherer, M. Anton, U. Schillinger, J. Henkel, C. Bergemann, A. Kruger, B. Gansbacher, C. Plank, Gene Ther. 2002, 9, 102), and immunoassay; B. Q. Sun, W. Z. Xie, G. S. Yi, D. P. Chen, Y. X. Zhou, J. Cheng, J. Immunol. Method. 2001, 249, 85. Magnetic nanosilica drug carriers can respond to external magnetic fields and thereby assist bioimaging, magnetic targeting agent to carry drug and delivery.

Some kinds of magnetic nanosilicas have been shown to have the potential for use in treatment of cancer; F. G. Xu, Q. Y. Ma, H. C. Sha, Crit. Rev. Ther. Drug Carr. Syst. 2007, 5, 445, M. W. Wilson, R. K. Kerlan, N. A. Fidleman, A. P. Venook, J. M. LaBerge, J. Koda, R. L. Gordon, Radiology, 2004, 230, 287. The 3D cage type of cubic SBA-16 has been widely used as catalyst and adsorbent in fine chemical processes. SBA-16 has a 3D porous network which could provide extensive diffusional access to some drug molecules.

Many obstacles must be overcome to attain a magnetic delivery system that delivers adequate amounts of curcuminoids to cancer cells in the human body. For example, a magnetic structured silica drug carrier for curcumin must have a suitable pore size for uptake, transport and subsequent release of curcumin at a target site as well as a suitable pore size to accommodate magnetic particles. These problems include solving the burst release problem, finding a suitable pore size for SPION and curcumin loading, and developing a suitable method for making a structured silica-SPION-curcumin composition.

Burst Release and Delivery to Target Site. Existing drug carriers contain a single kind of pore. For example, Q10 silica is one dimensional, MCM-41 is two dimensional, SBA-16 is three dimensional. While these carriers are reported to carry different kinds of drugs, they suffer from the problem of "burst release". Burst release results in premature or over-release of a drug during its transit to a target site in the body, such as a tumor site. Burst release results in wastage of the drug during transit, exposure of the blood or non-target tissues to concentrations of the drug increasing the risk of side-effects, and the delivery of suboptimal dosage of the drug to the target site. Moreover, burst release increases the cost of pharmacological therapy as more drug and potentially a longer period of treatment is often required. A complementary problem to burst release is how to facilitate the release of curcumin once it reaches the target. A new curcumin carrier needed to be developed that can increase the percentage of curcumin loading, transfer the curcumin to a target site without substantial release, and then release curcumin into or around target cancer cells which often reside in a more acid environment than normal, non-cancerous cells.

SPION size and Curcumin Loading. The designing of magnetic and drug loading in a single entity is cumbersome and challenging and developing suitable pore sized magnetic drug carrier having a suitable pore size to load, transport and release antioxidant molecules such as curcumin at a targeted site has not been tried. Formulation of agglomerations of nanosilicas with suitable nanoclusters of $Fe_2O_3$ particles for these functions has not been reported. Development of nanosupports that facilitate drug-delivery and that provide useful magnetic properties for tumor imaging application is needed. In preferred embodiments curcumin can be loaded in the range between 0, 5, 10, 15, 20, 25, 30, 35, 40, 45, 50, 55, 60, 65, or 70 wt % at the maximum.

SPIONs Preparation Difficulties. The preparation of $Fe_2O_3$ in desired nanosizes (such as ≤30 nm) are current challenges in material chemistry. In order to control the particle size, several efforts have been made using several different techniques such as hot injection method, controlled thermal disintegration and sonochemistry, etc. The formation of nanoclusters of $Fe_2O_3$ over SiSBA-16, Q-10 silica and mesocellular foam have not been reported.

To address these disadvantages of conventional drug carriers, the inventors sought to develop a new kind of SPIONs/nanocarrier nanoformulation for drugs such as curcumin that would increase the percentage of drug loading, for targeted drug delivery and tumor imaging capability. The above mentioned shortcomings, disadvantages and problems are addressed herein and which will be understood by reading and studying the following specification.

BRIEF SUMMARY OF THE INVENTION

The inventors provide a new way to deliver curcumin that effectively reduces the viability of cancer cells (MCF7 cells). In addition, they provide curcumin-loaded mesocellular foam silica nanoparticles impregnated with $Fe_2O_3$ allowing these nanoparticles to have a dual functions as chemotherapeutic drug carriers and as magnetic nanomaterial for imaging or targeting purposes.

The invention provides a composition which enhances and bioavailability of curcumin at target tissues and provides for imaging site-specific uptake of curcumin. Curcumin has poor pharmacokinetic properties as it is relatively insoluble in aqueous media including blood plasma and tissue fluids. Treatment methods using curcumin also suffer from a lack of an ability to track tissues that take up curcumin. The invention provides a way to traffic and deliver larger amounts of curcumin to a target tissue by including it as a cargo or payload in or on a nanosilica carrier, such as one based on SBA-16, Mesocellular foam, and/or Q-10 silica that also incorporates superparamagnetic iron oxide nanoparticles ("SPIONs"). The invention permits magnetic direction of the nanosilica-SPION-curcumin particles to target tissues such as those containing cancer cells for curcumin delivery.

In a first embodiment, the invention is directed to a composition comprising a platform of one or more types of nanoporous structured silica, at least one kind of magnetic nanoparticles in an amount ranging from about 5, 10, 15, 20, 25 to about 30 wt % based on total weight of the composition, and at least one curcuminoid. The platform of structured silica includes one or more of SiSBA-16, Q-10 silica, mesocellular foam (MSU-foam, mesocellular silica foam), silicalite, mesosilicalite, mesoporous silica, amorphous silica, SiKIT-6, ULPFDU-12 or SiMCM-41. The nanocarriers can also include high silica zeolites involving small, medium or large pore zeolites including ZSM-5, mordenite, Beta, HY, ZSM-11, ZSM-12, ZSM-22, and ZSM-23. The nanocarrier can also include carbon based nanocarriers such as mesocarbon, graphene oxide etc.

The composition of may contain magnetic particles, which are preferably superparamagnetic iron oxide nanoparticles ("SPIONS") which are non-toxic compared to other magnetic materials based on high concentration of cobalt and nickel. The composition may contain SPIONS made of magnetite $Fe_3O_4$ and/or its oxidized form maghemite or $\gamma$-$Fe_2O_3$.

The magnetic nanoparticles in the composition of the first embodiment above may contain $Fe_2O_3$ or a mixture of $NiFe_2O_4$, $CuFe_2O_4$, $MnFe_2O_4$ or $CoFe_2O_4$ and have an average particle size ranging from about 7, 8, 9, 10, 11, 12, 13, 14, 15, 16, 17 to about 18 nm when the structure silica is MSU-foam; about 9, 10, 11, 12, 13, 14, 15, 16, 17, 18, 19, 20 to about 21 nm when the structure silica is SiSBA-16 or a mesoporous silica; or about 10, 11, 12, 13, 14, 15, 16, 17, 18, 19, 20, 21, 22, 23, 24 or 25 nm when the structure silica is Q-10 or an amorphous silica. These ranges include all intermediate values and subranges.

The curcuminoid in the composition is preferably curcumin or a mixture of curcuminoids containing curcumin. Curcuminoids include as curcumin as well as demethoxycurcumin and bisdemethoxycurcumin and their geometrical isomers and metabolites. Preferably, a curcuminoid is incorporated or associated into the composition through an equilibrium or enforced adsorption technique.

In some embodiments of the composition of embodiment 1, the magnetic nanoparticles and/or curcuminoids and/or silica particles may be coated, covered with or otherwise incorporated into a polymer. Such polymers include so-called smart polymers such as pH- or temperature sensitive polymers that degrade at a pH or temperature around a tissue site containing cancer cells. In some embodiments, one or more components of the composition is functionalized with chitosan, polyacrylic acid, PLGA or another agent to increase its biocompatibility in vivo.

The composition as described above may also include a chemical or biological targeting agent, such as an antibody or other ligand that binds to a tumor-associated antigen or tumor marker or to markers characteristic of a target cell or tissue or characteristic of, or specific to, various types or subtypes of cancers, neoplasms or tumors.

The composition of the first embodiment above may exhibit a degree of magnetization (M, emu/g) as measured by vibrating sample magnetometry (VSM) greater than an otherwise identical composition wherein the platform of structured silica consists of SiSBA-16, Q-10 silica, mesocellular foam, silicalite, mesosilicalite, SiKIT-6, ULPFDU-12 or SiMCM-41. Preferably, the composition will contain MSU-foam, SiSBA-16 or a mesoporous silica, or Q-10 or an amorphous silica rather than Silicalite, SiKIT-6, ULPFDU-12 or SiMCM-41.

The composition of the first embodiment above may exhibit a percentage of cumulative curcuminoid release, in phosphate buffered saline (PBS) at pH 5.6 and 37° C. over 3 hours, greater than an otherwise identical composition wherein the platform of structured silica consists of SiSBA-16, Q-10 silica, mesocellular foam, silicalite, mesosilicalite, SiKIT-6, ULPFDU-12 or SiMCM-41. Representative values for cumulative release range from about at least 10, 15, 20, to about at least 25%. Preferably, the composition will contain MSU-foam, SiSBA-16 or a mesoporous silica, or Q-10 or an amorphous silica rather than Silicallite, SiKIT-6, ULPFDU-12 or SiMCM-41.

Another embodiment of the invention is a method for treating a cancer, neoplasm, or tumor comprising administering the composition described by the embodiments above to a subject in need thereof. The composition may be administered by any route that contacts it with the target tissue or cells. For example, it may be administered orally, intragastrically, intraintestinally, intraluminally, or rectally for cancers of the gastrointestinal tract. Other routes include but are not limited to topical, oral or nasal (including by inhalation), vaginal, parenteral (including topical, subcutaneous, intramuscular and intravenous) administration. The composition may also be administered in situ into or around a cancer, neoplasm, or tumor.

In some embodiments the composition will be magnetically guided to a target in the body of the subject after administration. In other embodiments, the composition may be functionalized, for example, with a ligand that binds to a tumor-associated antigen to enable it to selectively bind and accumulate at tumor sites.

In other embodiments, once the composition has reached its target tissue or target cancer cells it may be used to induce hyperthermia by application of radiation that releases heat when it contacts the magnetic particles in the composition. Advantageously this heat may inhibit cancer cell growth or serve to release curcumin and other drugs, when present in the composition, into or around the cancer cells, for example, when a smart or temperature-sensitive polymer is used to coat the curcumin or nanoparticles.

Another embodiment of the invention is a method for detecting cancer, neoplasm, or tumor cells that includes administering the composition of embodiments above that contains at least one agent that binds to or otherwise targets cancer, neoplasm, or tumor cells to a subject suspected of having a cancer, neoplasm, or tumor, detecting the magnetic nanoparticles using nuclear magnetic resonance (NMR) or X-ray imaging, selecting a subject in which the magnetic nanoparticles display and abnormal accumulation, localization or distribution compared to a control subject not having a cancer, neoplasm, or tumor; and treating the selected subject for the cancer, neoplasm, or tumor. This method may involve impregnating nanostructured pore surfaces of the platform of structured silica with magnetic nanoparticles, calcining the impregnated platform of structured silica, and adsorbing the curcuminoid to the calcined platform of structure silica and magnetic nanoparticles. In some embodiments calcining occurs at or between 450, 500, 550, 600, 650, 700, 750, 800, 850, 900 or 950° C. In this embodiment a platform of structured silica is at least one of MSU-foam, SiSBA-16 or a mesoporous silica, or Q-10 or an amorphous silica; the magnetic nanoparticles are SPIONS. One or more curcuminoids, preferably curcumin or a mixture containing curcumin is used for this embodiment. In some embodiments the curcuminoid comprises >0, 10, 20, 30, 40, 50, 60, 70, 80, 90, 95 or 100 wt % curcumin and may be adsorbed through an equilibrium or enforced adsorption technique.

BRIEF DESCRIPTION OF THE SEVERAL VIEWS OF THE DRAWING(S)

FIG. 1. X-ray diffraction pattern of curcumin/10 wt % SPIONs loaded over different nanocarriers; (a) curcumin, (b) Q-10, (c) Si-MCM-41, (d) Si-SBA-16, (e) mesocellular foam, (f) Si-KIT-6, (g) ULPFDU-12 and (h) Silicalite, respectively.

FIGS. 2A-2B show the $N_2$ adsorption isotherm of parent and 10 wt % Fe impregnated Q-10 silica, Si-MCM-41, SiSBA-16, MSU-foam, and SiKIT-6 silica.

FIGS. 2C-2D show the pore volume and pore width of parent and 10 wt % Fe impregnated silica nanocarriers. The BET surface area and pore structure, including pore surface area, pore volume and average pore diameter, of different nanocarriers are shown in Table 1.

Figure 3:
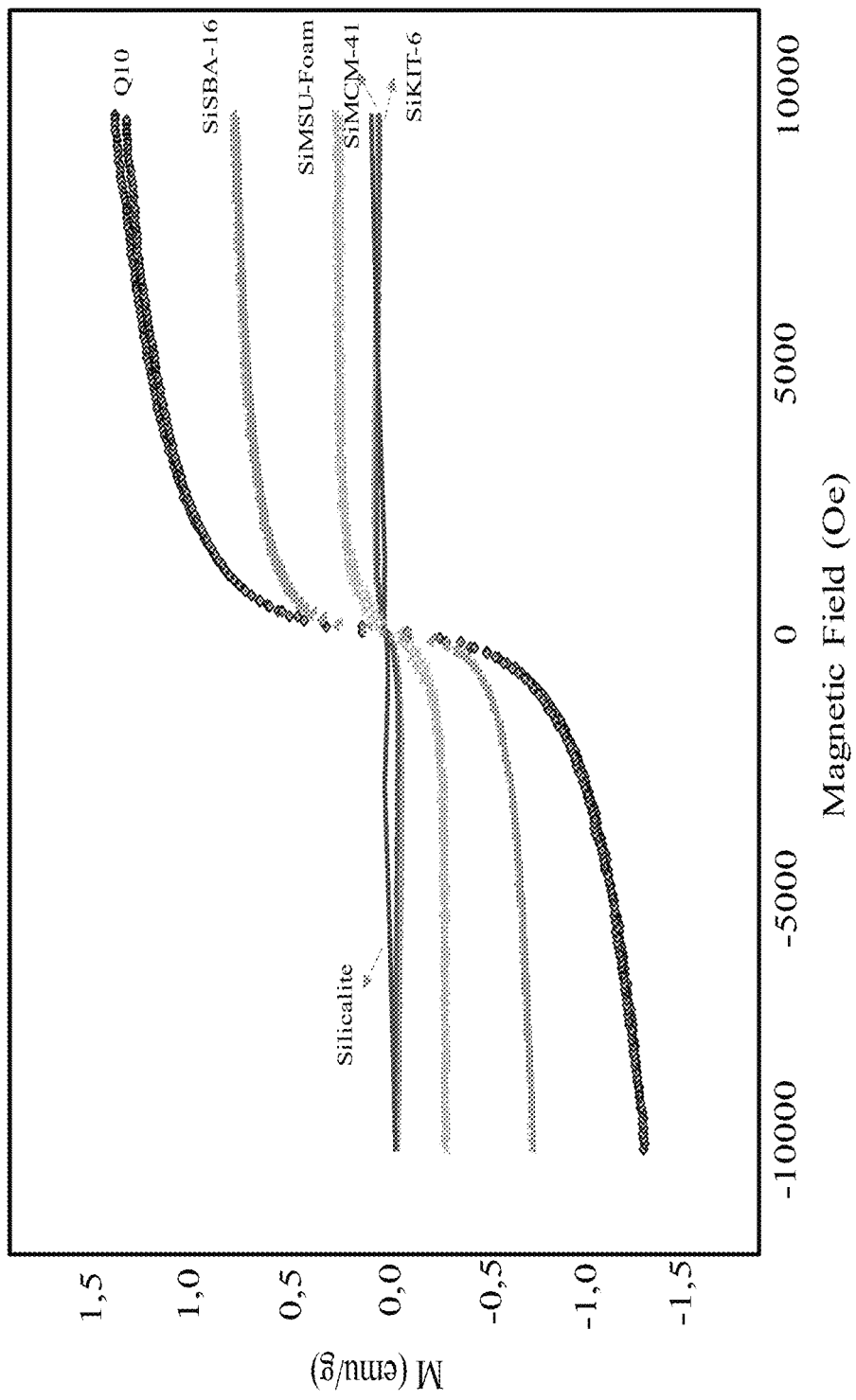

FIG. 3. The magnetic properties of 10 wt % SPIONs loaded over different nanocarriers.

Figure 4:
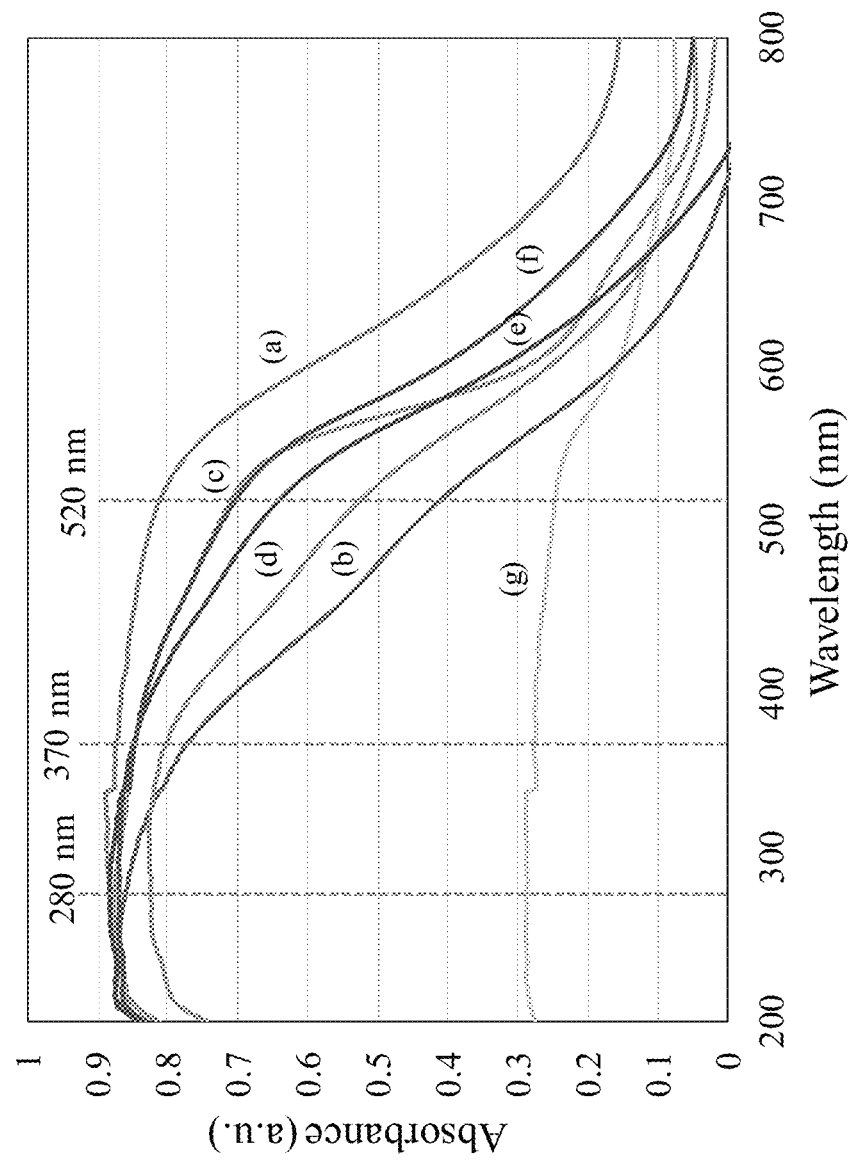

FIG. 4. Drs UV spectra of 10 wt % SPIONs loaded over different nanocarriers: (a) Q-10, (b) Si-MCM-41, (c) Si-SBA-16, (d) MSU-foam, (e) Si-KIT-6, (f) ULPFDU-12 and (g) Silicalite, respectively.

Figure 5:
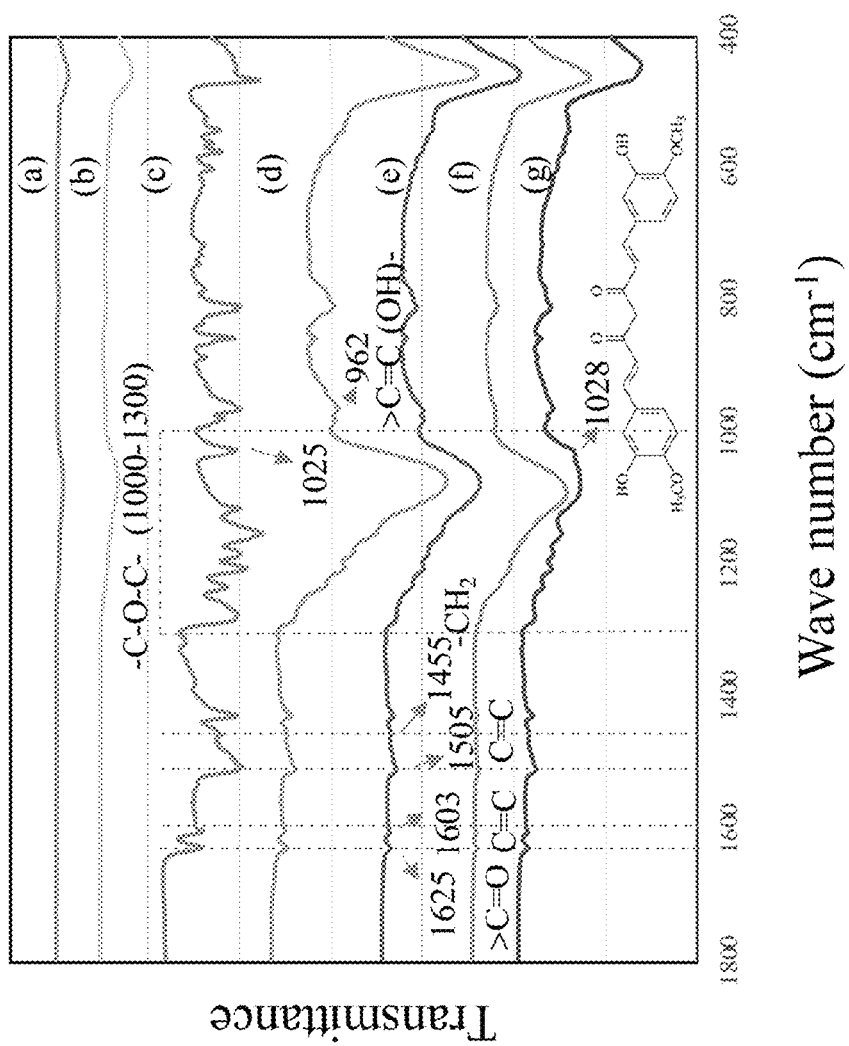

FIG. 5 shows the FTIR spectra of (a) Q-10 silica, (b) SPIONs/Q-10, (c) Curcumin, (d) Curcumin/Q-10, (e) Curcumin/SPIONs/Q-10, (f) Curcumin/SPIONs/MSU-foam and (g) Curcumin/SPIONs/SiSBA-16, respectively. The chemical structure of curcumin is shown at the bottom of the panel.

FIGS. 6A-6F. SEM micrographs based on comparative surface morphological features of 10 wt % SPIONs loaded over magnetically active nanocarrier. FIG. 6A: Q-10 silica; FIG. 6B: SPIONs/Q-10; FIG. 6C: SiSBA-16; FIG. 6D: SPIONs/SiSBA-16; FIG. 6E: mesocellular foam and FIG. 6F: SPIONs/MSU-foam, respectively.

FIGS. 7A-7F. Magnified SEM micrographs based on comparative surface morphological features of 10 wt % SPIONs loaded over magnetically active nanocarrier. FIG. 7A: Q-10 silica;

FIG. 7B: SPIONs/Q-10; FIG. 7C: SiSBA-16; FIG. 7D: SPIONs/SiSBA-16; FIG. 7E: MSU-foam; and FIG. 7F: SPIONs/MSU-foam, respectively.

Figure 8A:
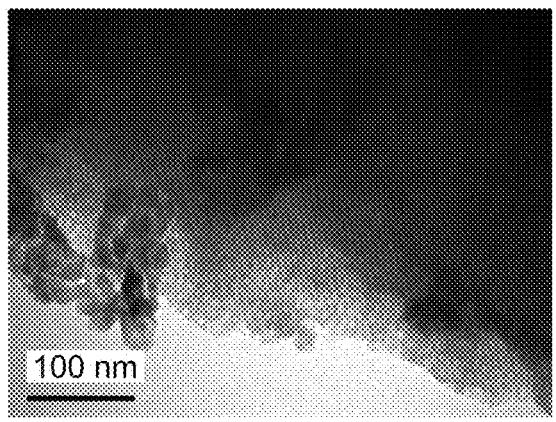
Figure 8B:
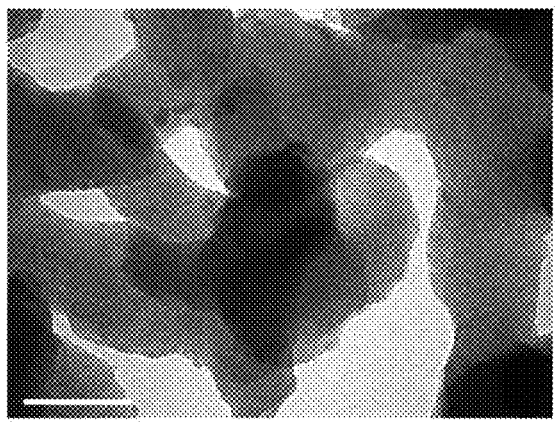
Figure 8C:
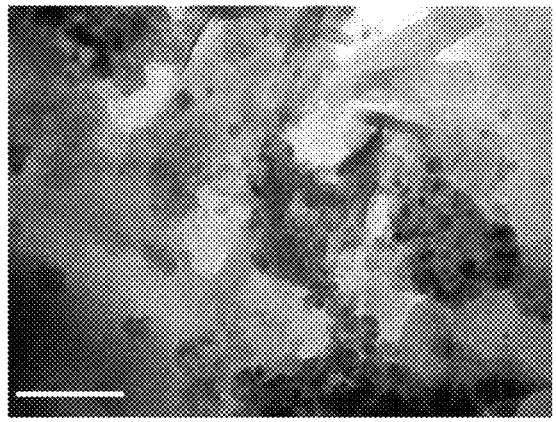
Figure 8D:
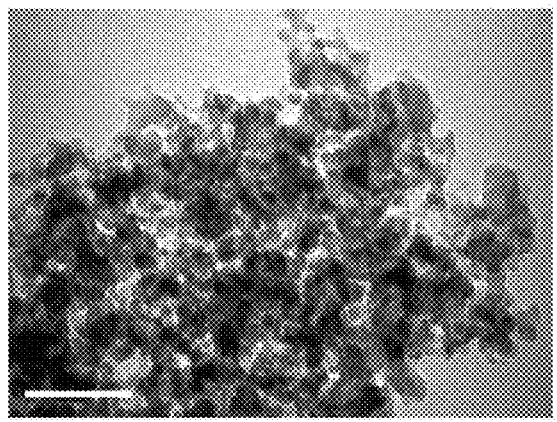
Figure 8E:
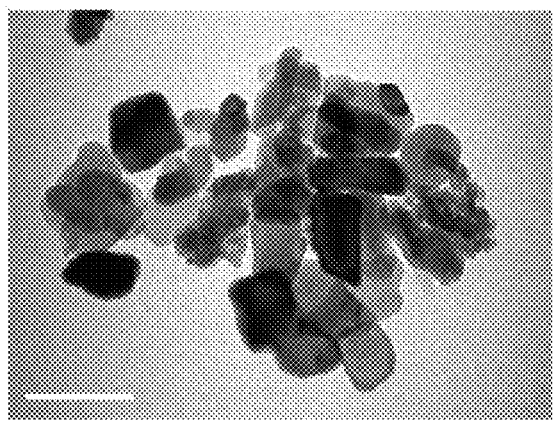

FIGS. 8A-8F. TEM images and average size of SPIONs. FIG. 8A: Fe/Si-SBA-16; FIG. 8B: Fe/Si-MCM-41; FIG. 8C: Fe/Q-10; FIG. 8D: Fe/MSU-Foam; FIG. 8E: Fe/Silicate; and FIG. 8F: bar graph of average size measurement with standard deviation for each specimen. Ten or more than ten particles were taken for size estimation and shown in the form of average size. Two ranges of particles were found: one small sized (FIG. 8F, blue/left bars) and the second large sized (green/right bars). The scale bars correspond to 100 nm.

FIG. 9. Pictorial representation of curcumin adsorption over SiSBA-16 nanocarrier (a-e) and SPIONs/SiSBA-16 (f j) at 30-390 µg/ml curcumin/nanocarrier in methanol-phosphate buffered saline (PBS) mixture stirred for 24 h.

Figures 10C, 10D:
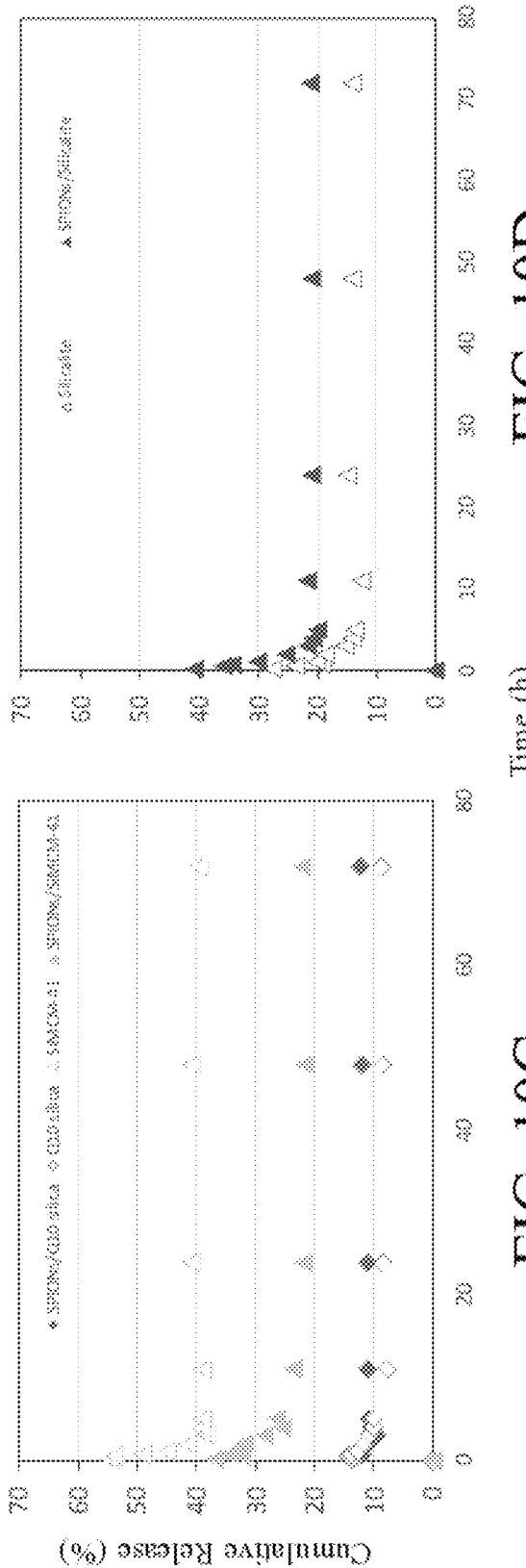

FIGS. 10A-10D. Curcumin release profile in nanosilicas with, or without SPIONS, in PBS solution (pH 5) for 3 h. Nanocarrier supports (powdered form): MSU-foam and SiSBA-16 (FIG. 10A), Si-KIT-6 and ULPFDU-12 (FIG. 10B), Q-10 and siMCM-41 (FIG. 10C) and Silicalite (FIG. 10D).

Figure 11:
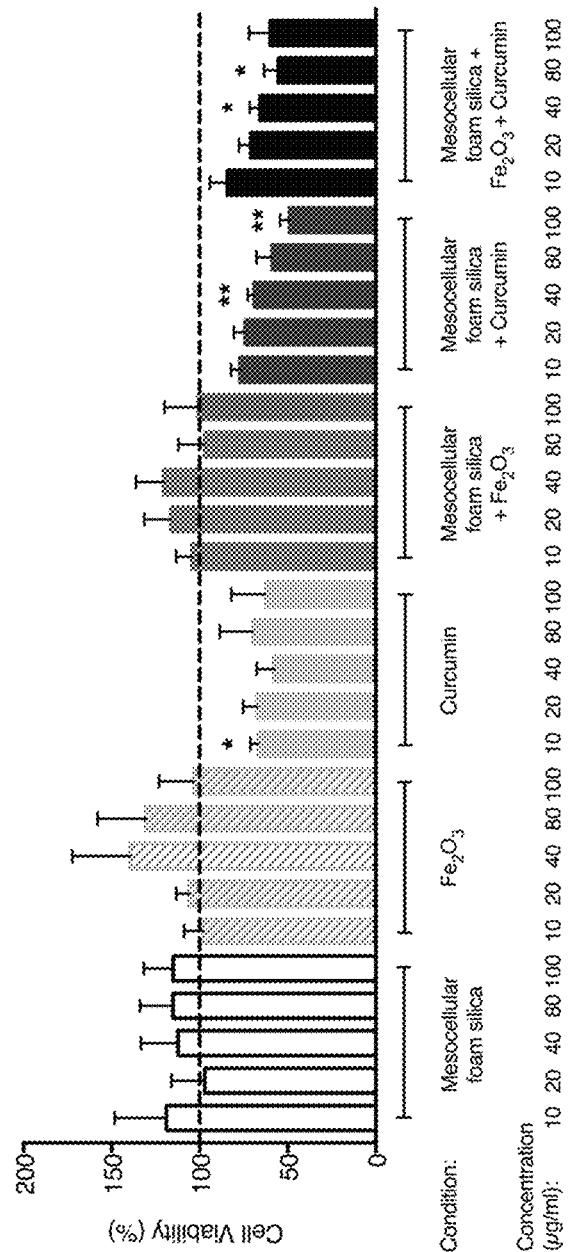

FIG. 11. SPIONs/MSU-foam loaded with curcumin significantly reduces cell viability. Percentage of cell viability with the following treatments: mesocellular foam silica ($1^{st}$ set), $Fe_2O_3$ (2nd set), curcumin ($3^{rd}$ set), mesocellular foam silica+$Fe_2O_3$ (4th set), MSU-foam silica+curcumin ($5^{th}$ set), and MSU-foam silica+$Fe_2O_3$+curcumin ($6^{th}$ set). Treatment concentrations were 10, 20, 40, 80, and 100 µg/ml for 24 h (n=5 independent experiments). Dashed line represents control, which is set as 100% cell viability. Error bars, ±SEM. *$P<0.05$;**$P<0.01$ versus control. This study is in progress.

FIG. 12A. Graphic depiction of magnetically inactive SPIONS/SiMCM-41 and magnetically active SPIONS/SiSBA-16 and SPIONS/MSU-foam. Schematic representation shows the nature of SPIONs deposition over different structured silicas.

Figure 12B:
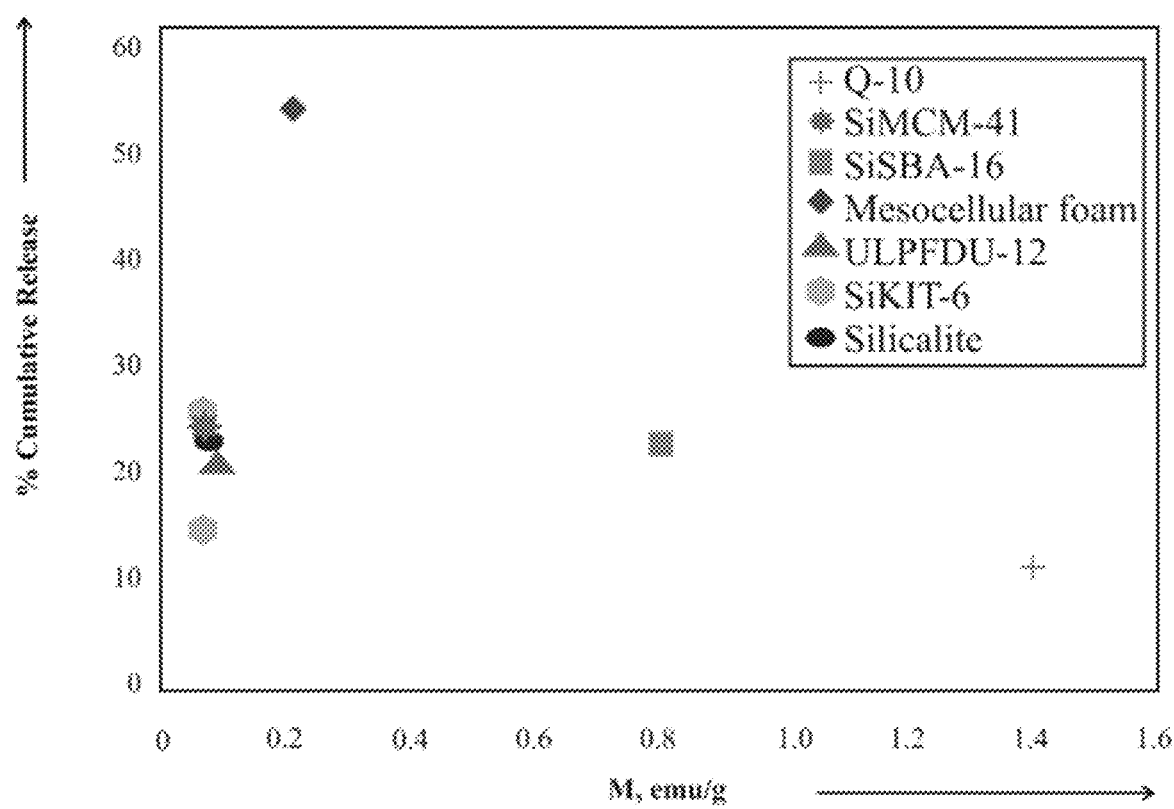

FIG. 12B. Cumulative release profiles of curcumin-loaded SPION/silica nanoparticles versus magnetization.

DETAILED DESCRIPTION OF THE INVENTION

Structured Silicas. The structured silicas are tested as nanocarriers in biomedical applications such as targeted oriented drug therapy, diagnostic purpose, stem cell and bioengineering. Mesoporous silicates, such as MCM-41 and SBA-15 are porous silicates with huge surface areas (normally ≥1,000 m²/g), large pore sizes (2 nm≤size≤20 nm) and ordered arrays of cylindrical mesopores with very regular pore morphology. Other mesotextured silicas include cubic SBA-16 and MCM-18. In some embodiments microstructured, mesoporous or macroporous silicas or mixtures thereof may be used. Most microporous silicas have average pore diameters of less than 2, 1.75, 1.5, 1.25, 1, 0.75, 0.5 or 0.25 nm. Most mesoporous silicas will have average pore diameters ranging from ≥2, 3, 4, 5, 6, 7, 8, 9, 10, 15, 20, 25, 30, 35, 40, 45 or 50 nm. Most macroporous silicas will have average pore diameters of >50, 60, 70, 80, 90 or 100 nm.

The possibility of silane functionalization of structured silicas or functionalization with chitosan has led the applications to expand beyond catalysis in fine chemical synthesis to magnetic, optical, battery and dielectric applications.

Nanocarriers used in the invention include (i) Q-10, (ii) SiSBA-16, (iii) mesocellular foam (MSU-F or MSU-foam), (iv) SiMCM-41, (v) ULPFDU-12, (vi) SiKIT-6 and (vii) silicalite. The structured silica can also be derived from micro-meso Silicalite/SiMCM-41, or different high ratio zeolite based composites. A zeolite can be ZSM-5, beta, USY, ZSM-11, silicalite, or other similar compounds. Other mesoporous silica materials having pore diameters between 2, 5, 10, 15, 20, 25, 30, 35, 40, 45 and 50 nm may also be used in some embodiments of the invention.

Nanoparticles generally refer to particles having average diameters ranging from about 1 to 100 nm, for example, 1, 2, 5, 10, 20, 50, <100 or 100 nm (or any intermediate value or subrange thereof). In some embodiments, the nanoparticles of the invention will have average diameters less than 50, 40, 30, 20, 10 or 5 nm. Average diameters may be measured by methods known in the art including by scanning electron microscopy ("SEM").

SPION or Superparamagnetic iron oxide nanoparticles. SPIONs are composed of magnetite or iron oxide which is degradable in the body and non-toxic compared to other magnetic materials such as cobalt and nickel. The main forms of magnetite are $Fe_3O_4$ and its oxidized form maghemite or $\gamma$-$Fe_2O_3$.

SPIONs may be produced by methods known in the art, for example, as described by Sun et al., J, American Chemical Society, 2002, 124, 8204. SPIONs may comprise one or more coatings or may be incorporated into micelles or liposomes to enhance desirably pharmacokinetic properties including biological half-life, biocompatibility, and targeting. The compositions of the invention contain SPIONs of a size compatible with in vivo administration and desired targeting functionality. Some representative SPION particle sizes range from about 1, 2, 5, 10, 20, 30, 40, 50, or 60 nm. A composition of the invention may contain a single size or single size distribution of SPIONs or may contain two or more sizes or size distributions. For example, various mixtures of large SPIONs ranging from about 10 to 60 nm in average size and small SPIONs ranging in size from about 2 to 22 nm may be used as described in Table 1-2. Mixtures of SPIONs of different sizes permit tuning of a biological responses or imaging functions. In some embodiments, a coprecipitation technique can be followed to form metal oxide composite with Ni or Cu or Mn and Co nanoparticle to form respective $MFe_2O_4$ to enhance imaging capacity by increasing magnetization property.

In some embodiments the core of the SPIONs may be magnetite which is covered with one or more shells, for example, a polymer shell or a gold or metal shell. SPIONs may also be incorporated into, or coated with, one or more polymers including smart, pH-sensitive, or temperature-sensitive polymers.

Functionalized super paramagnetic iron oxide nanoparticles (SPIONs) may be used in accordance with one or more embodiments of the invention, for example, a SPION (or other components of a composition of the invention) may be functionalized with one or more curcuminoids, or with a combination of one or more curcuminoids and a targeting ligand such as an antibody that binds to a tumor-associated antigen. In some embodiments SPIONs may be conjugated to targeting moieties such as ligands that bind to, or agents that are internalized by, tumor or cancer cells or by other target molecules, receptors, cells or tissues.

The content of SPIONS, porous silica, and curcumin in a composition according to the invention may be selected based on its intended use. However, some general content ranges for these components include from about 1, 2, 3, 4, 5, 6, 7, 8, 9, 10, 11, 12, 13, 14, 15, 16, 17, 18, 19 to about 20 wt % SPIONS, from about 80, 81, 82, 83, 84, 85, 86, 87, 88, 89, 90, 91, 92, 93, 95 to about 95 wt % porous silica, and a curcumin adsorption to the silica-based nanocarrier of 10, 15, 20, 50, 100, 120, 150, 200, 210, 220, 250, 300, 310, 320, 330, 340, 350, 360, 370, 380, 390, 400, 420, to about 450 µg/ml curcuminoid. These ranges are based on adsorption in PBS containing 10 wt % methanol after 24 hr and include all intermediate values and subranges.

In embodiments for use in vivo, curcuminoid adsorption to a nanocarrier may be performed in a medium not containing methanol which can be toxic in vivo. For example, a solvent such as acetone, ethanol, DMSO and diemethylformamide (or a nontoxic or pharmaceutically acceptable organic or aqueous solvent) may be used in place of methanol. For particular applications, an amount of curcumin or other curcuminoid may be selected that when administered in vivo inhibits the activity of histone deacetylases: HDAC1, HDAC3, HDAC8, transcriptional co-activator proteins such as p300 histone acetyltransferase, or arachidonate 5-lipoxygenase by at least 10, 20, 30, 40, 50, 60, 70, 80, 90 or >90%.

Curcumin has the following structure:

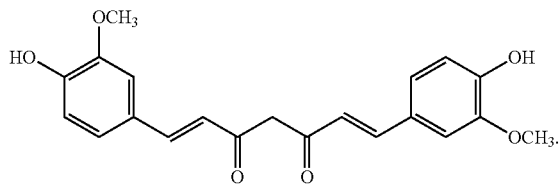 [SMILES: COc1cc(/C=C/C(=O)CC(=O)/C=C/c2ccc(O)c(OC)c2)ccc1O]

A curcuminoid is a linear diarylheptanoid. This class of compounds includes curcumin in both its keto and enolate forms as well as curcumin derivatives such as demethoxycurcumin and bisdemethoxycurcumin and their geomentrical isomers and metabolites including sulfate conjugates and glucoronides. Other examples of curcumin derivatives or analogs include those described by Raja, et al., U.S. Pat. No. 9,447,023 B2, Raja, et al., U.S. Pat. No. 9,650,404 B2, Johnson, et al., U.S. Pat. No. 9,556,105 B2 or Vander Jagt, et al., U.S. Pat. No. 9,187,397 B2 (all incorporated by reference); especially for their descriptions of curcuminoid formulas and various chemical species of curcuminoids.

Mixtures of curcuminoids are also contemplated such as one isolated from rhizomes of turmeric comprised of Curcumin (75-81%), Demethoxycurcumin (15-19%) and Bisdemethoxycurcumin (2.5-6.5%). The content of any one of a curcuminoid in a mixture may range from about 0 to about 100 wt %, for example, 10-90 wt %, 20-80 wt %, 30-70 wt %, 40-60 wt %., 50 wt %, 40 wt %, 33.3 wt %, 30 wt %, 20 wt %, 10 wt % or 5 wt % or 1 wt %. A mixture may contain two, three or more different curcuminoids.

Curcumin may be present in a crystalline or amorphous form or in a mixture of both crystalline and amorphous forms, for example at a ratio of 1-99 wt %:99-1 wt %, 10-90 wt %:90-10 wt %:20-80 wt %:80-20 wt %, 30-70 wt %:70-30 wt %, 40-60 wt %:60-40 wt % or about 50 wt %: about 50 wt % (or any intermediate ratio of crystalline: amorphous forms. In some embodiments disclosed herein, curcumin will be in an amorphous form to increase its solubility.

Curcumin and its derivatives are known for their antimicrobial, anti-oxidative, anti-inflammatory, and anti-cancer properties such as malignancies in the brain or nervous system. Curcumin has also been proposed as an agent to treat oxidative stress, such as oxidative stress in the brain, and for treatment of neurodegenerative disease like Alzheimer's disease ("AD") or Parkinson's disease ("PD"); Lee, et al., Curr. Neuropharmacol. 2013 July; 11(4):338-378 (incorporated by Reference).

Curcumin may also be functionalized or prepared as a conjugate with another moiety to modify or improve its pharmacokinetic properties. For example, curcumin can be adsorbed through functionalization to a silane, carboxylic acid, or biotin. Moreover, biocompatibility of curcumin/SPIONs/mesosilica nanoformation can be increased by the modification with chitosan, or poly (D,L-lactide-co-glycolide), or polyethylene glycol.

Smart Polymers. These represent a combination of nano- or micro-sized solid functional materials with one or more polymers. For example, a magnetic material, such as a SPION, may be incorporated or dispersed into a polymer composite. Anisotropic properties may be conferred on the composite structure or particles by application of a magnetic field during crosslinking or condensation of the polymer. In some embodiments of the invention, SPIONs will be incorporated into, or covered with, a polymer to form nanoparticles with a polymer coating that can shield the body from direct exposure to the SPIONs or control the rate of exposure and subsequent elimination of SPIONs. These nanoparticles may be produced with anisotropic magnetic properties. In some embodiments, smart polymer coatings can be pre-applied to curcumin before or during loading. In other embodiments smart polymers can cover the SPIONs and silica nanoparticles.

In other embodiments, a curcuminoid or curcuminoid particles may be incorporated into, or covered with, a smart polymer that provides for controlled release of the curcuminoid. Smart polymer matrices release drugs by a chemical or physiological structure-altering reaction, often a hydrolysis reaction resulting in cleavage of bonds and release of drug as the matrix breaks down into biodegradable components. While natural polymers may be used, artificially synthesized polymers such as polyanhydrides, polyesters, polyacrylic acids, poly(methyl methacrylates), and polyurethanes may be used as well as conventional pH- and temperature-sensitive polymers and copolymers.

A pH-sensitive polymer may be chosen to encapsulate or cover a curcuminoid, SPIONs or silica particles, and dissolve at a pH or temperature around a tumor, and preferentially release the curcuminoid in or around a tumor, for example, in a tumor that is present in an acidic microenvironment. One example of a pH-sensitive polymer would be a polymer than degrades faster in a more acidic environment around a cancer cell than at a pH around non-cancerous cells. Such polymers may be selected depending on the type of cancer cell, its location and the metabolic status of the patient so that a curcuminoid will be preferentially released in the relatively more acidic environment around the cancer cell or under other conditions around or applied around target cells or in target tissues. Representative pH for tumor microenvironments include 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, or <7.6. These generally lower pH or more acidic pHs are attributed to glycolytic activity and lactate release or to more rapid division by cancer cells. The microenvironments around many non-cancerous cells will be higher than those around cancer cells and may fall within a range of about 7.2, 7.3, 7.4, 7.5, 7.6, 7.7, 7.8, 7.9, or 8.0.

Hydrophilic, amorphous, low-molecular-weight polymers containing heteroatoms (i.e., atoms other than carbon) may provide for faster degradation. The rate of degradation may be controlled by adjusting the composition or thickness of the smart polymer to control the rate of release of curcuminoid at a target site. Smart polymers have been developed and are shown to respond to the external magnetic field as well to pH and temperature changes; pH- and thermal-responsive magnetic microcarriers for curcumin are described by. E. A. M. S. Almeida, I. C. Bellettini, F. P. Garcia, M. T. Farinacio, C. V. Nakamura, A. F. Rubira, A. F. Martins, E. C. Muniz, *Curcumin-loaded dual pH—and*

*thermo-responsive magnetic microcarriers based on pectin maleate for drug delivery*; Carbohydrate Polymers 171 (2017) 259-266. Smart polymers also are described by, and incorporated by reference to, Filipcsei, et al., Adv. Polymer Sci. 206(1):137-189 (2007).

In some embodiments, the curcuminoid will be directly adsorbed, or non-covalently or covalently associated with the nanoporous silica and/or SPIONS. In other embodiments, the curcumin can be adsorbed or bound to the nanocarrier or SPIONs through functionalization of one or more components of the composition, such as by functionalization of curcumin, silica or SPIONS with silanes, carboxylic acid, or biotin/strepavidin. In other embodiments, the biocompatibility of curcumin/SPIONS/mesosilica nanocomposition can be increased by the functionalization of components of the composition with chitosan, or poly (D,L-lactide-co-glycolide), or polyethylene glycol.

Methods and agents suitable for functionalization of SPIONS and other nanoparticles are described by Rimonidini, http://_www.cost-newgen.org/wp-content/uploads/2015/12/23-Sofia-COST-2015-rimondini.pdf (incorporated by reference, last accessed Apr. 20, 2018) and by Lee, et al., J Nucl Med 2013; 54:1-7 DOI: 10.2967/jnumed.113.122267 (incorporated by reference), and Mishra, et al., Adv. Sci. 2017, 4, 1600279, DOI: 10.1002/advs.201600279 (incorporated by reference).

Targeting to tumor antigens. Ligands such as antibodies that recognize tumor-associated antigens (or molecules such as receptors expressed at higher than normal levels by cancer cells) may be used to functionalize the compositions of the invention. Tumor-associated antigens include oncofetal antigens, such as alphafetoprotein (AFP, associated with germ cell cancers or hepatocellular cancer) or carcinoembryonic antigen (CEA, associated with bowel cancer); tumor antigens such as CA-125 (ovarian cancer), MUC-1 (breast cancer), epithelial tumor antigen (ETA, associated with breast cancer), tyrosinase (associated with malignant melanoma), abnormal ras, p53 tumor antigens; abnormal proteins made by oncoviruses such as EBV or HPV; or abnormal cancer-associated glycoproteins or glycolipids. Ligands that bind to tumor-associated antigens may be conjugated to one or more elements of the composition of the invention, for example, to an iron oxide surfaces of SPIONS, by methods known in the art such as with a cleavable or non-cleavable linker, by tagging an element of the composition with biotin or (strep)avidin and the ligand with (strep)avidin or biotin, or by chemical conjugation Magnetic targeting of drugs is known in the art and is incorporated by reference to Chertok, et al., Biomaterials 29(4), February 2008, Pages 487-496 (brain cancer), Marcu, et al., Applied Surface Science 281, 15 Sep. 2013, Pages 60-65 (breast cancer), and Dames, et al., Nature Nanotechnology 2: 495-499 (2004)(lungs), each of which is incorporated by reference. The composition of the invention advantageously is used to target a curcuminoid to a cancer, neoplasm, or tumor. It may also be used to target the curcuminoid to other tissues including those of the enteral, urinary, or respiratory systems. In some embodiments, the composition of the invention will be magnetically targeted to a cancer site and the release of curcumin will also be controlled under the influence of a magnetic field. In some embodiments of the invention a biopolymer is used to improve SPIONs biocompatibility, targeted drug delivery capability, magnetically active for magnetic resonance imaging (MRI). In other embodiments, a biopolymer release drugs in a pH-dependent manner once magnetically localized to a tissue containing cancer cells.

Hyperthermia and hyperthermic treatment refer to subjection of a body or a portion thereof, to temperatures above 37° C., such as to temperature of 40° C. or more, including 41° C. or more, such as 42° C. or more, such as 40 to 45° C., for a desired amount of time, e.g., 1 min or longer, e.g., 5 min or longer, including 10 minute or longer, e.g., 1 minute to 2 hours, such as 5 minutes to 1 hour.

Inductive hyperthermia. Devices or methods useful for inductive hyperthermia are known. These methods may use current magnetic fields in combination with ferromagnetic nanoparticles such as SPIONs. Devices and methods for inducing hyperthermia are described by Kuroda, et al., Med. Biol. Eng. Comp. 37(3):2850290 (1999), by Araya, et al., OncoTargetsTher. 6:237-42 (2013), or by Zhao, et al., Rare Metals, vol. 25, issue 6, suppl 1, pp 621-625 (2006); which are incorporated by reference.

An anti-cancer agent (or anti-neoplastic agent or anti-tumor agent) encompasses all agents and therapeutics modalities known to one of skill in the art to ameliorate the symptoms in some manner of a cancer, neoplasm, or tumor. These include any agents, used alone or in combination with other agents or compounds, can reduce, ameliorate, trigger a state of remission of symptoms or markers associated with cancers, tumors, and the like, and can be used in methods and compositions provided herein.

A chemotherapeutic agent includes any material or compound used in the art for the treatment of cancer. Chemotherapy can be conducted with a large variety of agents and can include treatments with cisplatin, cisplatin-based compounds, carboplatin, mitomycin, vincristine, methotrexate, fluorouracil, calcium folinate, cytosine arabinoside, cyclophosphamide, epirubicin, etoposide, bleomycin A5, taxanes, mitoxanthrone, cylcophosphamide, topoisomerase inhibitors, angiogenesis inhibitors, cisplatin-based therapies, differentiation agents, signal transduction inhibitors, busulfan, doxorubicin rapid dissolution, etoposide, 5-fluorouracil, tamoxifen, their salts, and combinations thereof. Some embodiments of the invention will include compositions containing one or more chemotherapeutic agents in combination with curcumin or a curcumin derivative.

One or more anti-cancer or chemotherapeutic agents may be used in conjunction with a composition according to the invention. It may be administered before, simultaneously, or after the composition of the invention or may be incorporated into a composition of the invention along with a curcuminoid. It may also be coadministered in a composition similar to the invention where the curcuminoid is replaced by one or more anti-cancer agents.

Cancer refers to a general term for diseases caused by any type of tumor, including solid tumors or tumors of the blood, and neoplasms. As used herein, neoplasm refers to abnormal new growth, and thus means the same as tumor, which may be benign or malignant.

Treatment describes at least an amelioration of one or more symptoms associated with the condition afflicting the host is achieved, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g., prevented from happening, or stopped, e.g. terminated, such that the host no longer suffers from the side-effects or symptomatic side-effects of a treatment.

An anti-cancer treatment refers to any treatment designed to treat the cancer, tumor, or neoplasm by lessening or ameliorating its symptoms including its growth rate, ability to enter the circulatory system or lymph nodes, or to metastasize. Treatments that prevent the occurrence of cancer, tumor, or neoplasm or lessen its severity are also contemplated.

EXAMPLES

The inventors show in the following Examples that nanoporous silica hybridized to magnetic nanoparticles (SPIONs) and loaded with curcumin/SPIONs may be used for a dual purpose of drug delivery of curcumin and magnetic resonance imaging. As disclosed or shown by the following Examples, the inventors have developed multifunctional supermagnetic iron oxide nanoparticles (SPIONs) based structured silica such as spherical silica, SiSBA-16 and mesocellular foam, to provide an effective dual targeting magnetic nanomaterial for antioxidant (curcumin) delivery. A structured silica platform containing 10 wt % SPIONs was developed and provides an acquisition effect of curcumin in a range of about 30-390 μg/.

The effect of functionalization using different chain length of silanes and biocompatibility using chitosan fabrication were tested for controlled drug delivery.

Fe nanoparticles are incorporated into the structured silica and silicalite through an enforced adsorption method.

The morphological variation of developed hybrid drug were scrutinized using various physico-chemical techniques such as X-ray diffraction (XRD), surface area analysis (BET), FTIR, Scanning electron microscope (SEM) and Transmission electron microscope (TEM).

The drug loading and delivery at various times were studied using UV-Visible spectroscopy analysis. To investigate the cell viability effects, curcumin-loaded/$Fe_2O_3$ impregnated mesocellular foam silica nanoparticles which showed a high curcumin release effect were contacted with MCF7 cells in vitro to assess cell viability using the MTT assay.

Example 1

Nanoporous Silica Platforms and Silica-SPION-Curcumin Compositions

Various kinds of nanoporous silica platforms, namely Q-10, Si-MCM-41, Si-SBA-16, MSU cellular foam, Si-KIT-6, ULPFDU-12 and silicalite, were hybridized with 10 wt % Fe SPIONs to form magnetically responsive silica through enforced adsorption technique. Curcumin was loaded into or onto the magnetic silica through an equilibrium adsorption technique.

The phase, textural and morphological variation of developed magnetically responsive silica and curcumin functionalization was scrutinized using X-ray diffraction (XRD), surface area analysis (BET), Fourier transformed infrared spectroscopy (FT-IR), Scanning electron microscope (SEM) and Transmission electron microscope (TEM). The coordination of iron oxide over silica was studied using DRS-UV spectroscopy. The magnetization property was analyzed using Vibrating Sample Magnetometry (VSM). SPIONs loaded over Q-10, SBA-16 and MSU-Foam were found to be magnetically active, while Si-MCM-41, Si-KIT-6 and silicate were found to be magnetically inactive. 30-390 μg/ml of curcumin was loaded in 10% methanol in Phosphate buffered saline (PBS) mixture and the release study was carried out in PBS solution (pH 5.6) for 72 h at 37° C. The adsorption study shows that curcumin adsorption over SPIONs hybrid silica (Q-10 and SiSBA-16) was boosted and was not affected by iron oxide impregnation. The curcumin release study was compared in the absence and presence of SPIONs over silica.

These Examples shows that drug release sustained in the presence of SPIONs over silica than silica alone. $Fe_2O_3$ over MSU-Foam showed a highest percentage cumulative release of 53.2% for 72 h, while SiSBA-16 and Q-10 showed steady release with over 16% and 12% over 72 h, respectively. Further details of these Examples are provided below.

Experimental Section. The silica specified as CARiACT Q-10 with pore diameter of 18.6 nm was purchased from Fuji Silysia Chemical Ltd, while foam type mesosilica termed as (MSU-F) was obtained from Aldrich. The detailed synthesis procedure for the support Si-MCM-41, Si-SBA-16, Si-KIT-6, ULPFDU-12, and silicalite was provided in an earlier published article; V. Ravinayagam, B. Rabindran Jermy, Studying the loading effect of acidic type antioxidant on amorphous silica nanoparticle carriers, 19 (2017) 190.

Fe Loading Over Nanocarriers Through Enforced Adsorption Technique.

An enforced impregnation technique was used to impregnate $Fe_3O_4$ into the pores of structured silica. Before the impregnation procedure, in order to improve the impregnation, drying and vacuum treatment was performed to remove the pre-adsorbed moistures inside the pores. Alternatively, $Fe_3O_4$ impregnation can be performed through wet impregnation or can be incipient wetness route or can be incorporated during synthesis itself 10 wt. % loading of Fe was established by adding 0.7235 g of iron nitrate nonahydrate in 80 ml of water, followed by stirring till dissolution. Then 1.0 g (1,000 mg) of nanocarrier was subsequently added and stirred for 24 h at room temperature. After stirring, the material was dried without filtration at 120° C. for 3 h and the recovered material was further calcined at 500° C. for 2 h.

In an alternative process silica can be impregnated with metal oxides such as gold, titanium, nickel, copper, manganese or other metal/oxide nanoparticles to produce a composite having different diagnostic or other functional properties. For instance, the impregnation can be performed through coimpregnation of the silica with SPIONs and additional active metal oxides based on nickel. In other embodiments the calcination temperature of the mixture of $Fe_2O_3$/mesosilica may be selected within the range of about 300-800° C.

Curcumin adsorption through equilibrium adsorption technique. Curcumin adsorption over different nanocarriers and Fe impregnated nanocarriers was carried out through an equilibrium adsorption technique. 1.0 g (1,000 mg) of nanocarrier was taken and added in the solution containing 200-1,500 μg/ml of curcumin in 10% methanol in Phosphate buffered saline (PBS) mixture and stirred for 24 h. Then the solution was filtered, dried at room temperature. The percentage adsorption was calculated based on the equation:

Percentage of curcumin adsorption (%)=(Initial curcumin conc−Final curcumin conc)/Initial curcumin conc×100.

The final curcumin concentration was calculated based on the equation:

Final curcumin concentration=(Final absorbance value×Initial curcumin conc)/Initial absorbance value.

These results showed the final concentration of adsorption to range from 30-390 μg/ml of curcumin.

Curcumin release. A curcumin (drug) release study was carried out in PBS solution (pH 5.6) at 37° C. Specifically, for drug release study, 30 mg of (390 µg/ml curcumin/nanocarrier) sample was taken and dissolved in 50 ml of PBS (pH 5) solution in a conical flask. Then the temperature was raised to 37° C. and gradually stirred at 200 rpm for the following drug release study. At certain period, 10 ml of solution was withdrawn and replaced with equal volume of fresh PBS solution. Then the release amount was calculated based on the calibration curve at specified wavelength of 428 nm.

Characterization. The X-ray diffraction pattern for meso-structured silicas was analyzed using bench top Rigaku Multiplex system. The textural characteristics (surface area, pore volume and pore size distribution) were measured using an ASAP-2020 plus, accelerated surface area and porosimetry, Micromeritics, Norcross, GA, USA. The magnetic measurements were conducted with LDJ Electronics Inc. Model 9600 VSM in an applied field of 10 kOe. The calcined Fe/silica samples were measured using 60 mm dia integrating sphere equipped UV-Vis (Ultraviolet visible) V-750 diffuse reflectance spectroscopy (JASCO). Fe/silica and curcumin methyl and functional groups were identified using Fourier transform infrared spectroscopy (Perkin Elmer) equipped with attenuated total reflectance (ATR). The average size and the surface morphology of the as synthesized specimens were measured using transmission electron microscope (TEM, FEI, and Morgagni, Czech Republic) and scanning electron microscope (FE-SEM, TESCAN FERA3). SEM was performed at operating voltage of 20 kV and TEM at 80 kV. For SEM, the samples were mounted onto metallic stubs with a double-sided adhesive tape. Gold coating of a few nanometers was applied on specimens using sputter coating machine (Quorum, Q150R ES, UK) to avoid charging and capture high quality electronic micrographs. Low and high magnification SEM imaging was performed to capture the recognized features of the specimens. TEM samples were prepared by dropping particle dispersions onto carbon-coated Cu grids and air-dried before mounting into the microscope. Particle sizes were measured from electronic images using Gatan digital micrograph software. The data is presented in the form of average number for each specimen with a standard deviation.

Figure 1:
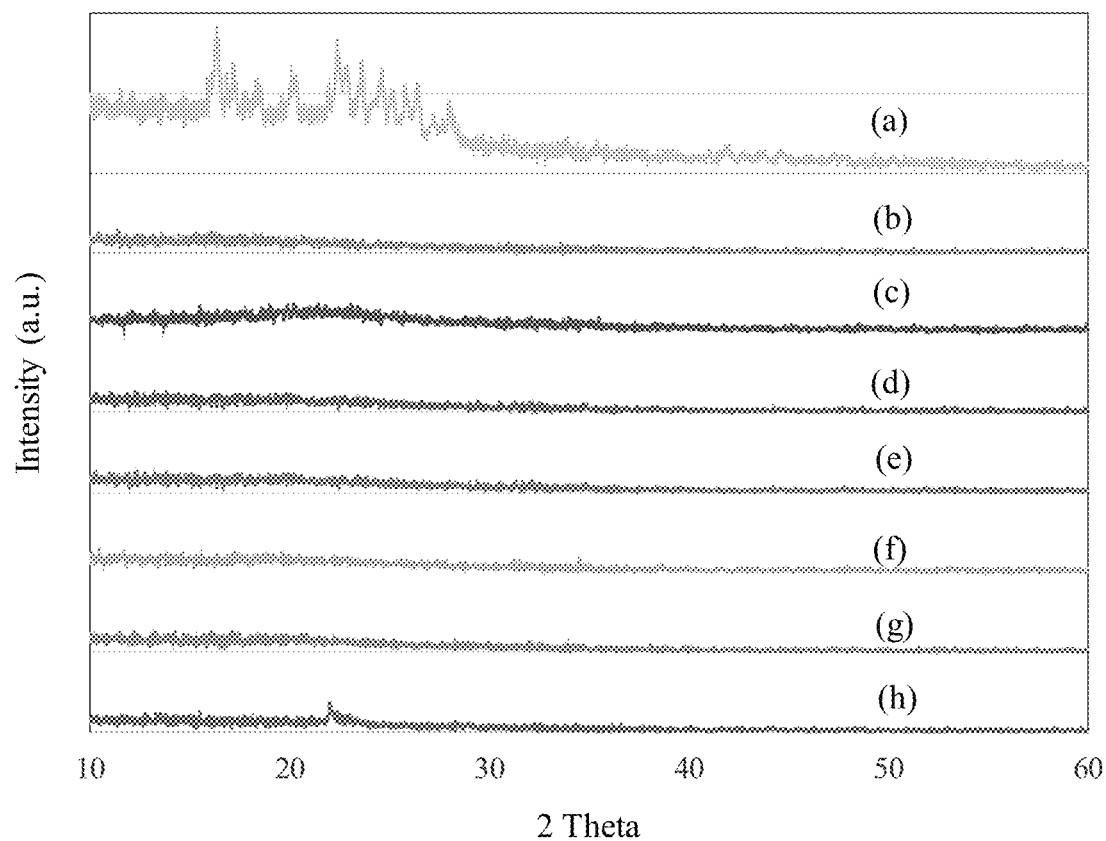

The X-ray diffraction patterns of pure curcumin and curcumin adsorption over 10 wt % SPIONs loaded over different nanocarriers are shown in FIG. 1: (a) pure curcumin, (b) Q-10, (c) Si-MCM-41, (d) Si-SBA-16, (e) Mesocellular foam, (f) Si-KIT-6, (g) ULPFDU-12 and (h) silicalite, respectively.

In the case of pure curcumin (a), various diffraction peaks over the 2 theta range 15-30° were observed indicating characteristics crystalline phase of curcumin; S. Mutalik, N. A. Suthara, R. S. Managuli, P. K. Shetty, K. Avadhani, G. Kalthur, R. V. Kulkarni, R. Thomas, *Development and performance evaluation of novel nanoparticles of a grafted copolymer loaded with curcumin*, Int J BiolMacromol. 86 (2016) 709-720.

In contrast, curcumin loading over SPIONs/different structured nanocarriers showed no such crystalline peaks indicating effective transformation of curcumin into amorphous state. These data show that apart from silicalite, such a noncrystalline state of curcumin was achieved over all types of structured silica irrespective of their structural domains of one dimension (1D), two dimension (2D), and three-dimension (3D).

Past work has attributed transformation of a crystalline drug to a noncrystalline amorphous form to the confinement of drug inside the geometrically constructed nanopores; F. Wang, H. Hui, T. Barnes, C. Barnett, C. Prestidge, Mol. Pharm. 7 (2009) 227-236. In particular, cubic cage nanopores of SBA-16 were reported to be effective for such crystalline transformation of drug to nanoform. In case of carvedilol molecules (CAR), the presence of cage type of 3D nanopores of SBA-16 was reported to thwart the transformation of the CAR molecules into crystalline state by preventing the extension of the crystal lattice inside the 3D nanopores; Hu, Z. Zhi, Q. Zhao, C. Wu, P. Zhao, H. Jiang, T. Jiang, S. Wang, 3D cubic mesoporous silica microsphere as a carrier for poorly soluble drug carvedilol, Micropor. Mesopor. Mater., 147 (2012) 94-101. Similarly, in the case of amorphous type of silicas, such as (b) Q-10 silica and (c) SiMCM-41 a characteristic broad peak of silica at about 2 theta range of 22° was not observed indicating effect of SPIONs impregnation.

The presence of $Fe_3O_4$ was expected to be observed at 2 theta value of 35.45°. However the XRD pattern of all SPIONs/nanocarriers showed no such peak, indicating weak and broadening of such peaks due to small nanosized $Fe_3O_4$ particles, which are attributed to the lack of crystallization at such nanopores of nanocarrier, see FIG. 1 (b)-(h).

In case of nanocarriers without SPIONS, typical isotherm patterns were observed. The mesocellular foam exhibited type IV isotherm due to cellular foam structure. In case of Si-SBA-16 and Si-KIT-6, H1 type isotherm appears indicating typical cubic cage type pores. The Si-MCM-41 exhibited reversible type IV isotherm pattern with uniform pore size distribution; see FIGS. 2A and 2C.

The textural changes in the absence, as shown in FIGS. 2A and 2C, and of SPIONs, as shown in FIGS. 2B and 2D, were evaluated using $N_2$ adsorption isotherm technique. FIGS. 2A-2B show the $N_2$ adsorption isotherm of parent and 10 wt % Fe impregnated Q-10 silica, Si-MCM-41, SiSBA-16, mesocellular foam, and SiKIT-6 silica. FIGS. 2C and 2D show plot pore volume ($cm^3/g \cdot nm$) against pore width (nm). Table 1 below describes the BET surface area and pore structure of different nanocarriers.

TABLE 1

Textural Properties of parent and 10 wt % Fe impregnated over different structured silica.

| Fe/Nanocarrier [wt % g$^{-1}$ support] | BET Surface area [m$^2$/g - support]$^a$ | Pore Surface Area [cm$^3$/g - support]$^b$ | Cumulative Pore Volume (cc/g) [cm$^3$/g - support]$^c$ | Average Pore Diameter [nm]$^d$ |
|---|---|---|---|---|
| Q-10 (1D) | 233 | 270 | 1.08 | 18.6 |
| 10 wt % Fe/Q-10 | 258 | 274 | 1.02 | 15.8 |
| Si-MCM-41 (2D) | 942 | 1200 | 0.88 | 3.7 |
| 10 wt % Fe/Si-MCM-41 | 951 | 1022 | 0.71 | 3.0 |
| Si-SBA-16 (3D) | 677 | 337 | 0.48 | 2.8 |
| 10 wt % Fe/Si-SBA-16 | 327 | 194 | 0.33 | 4.0 |

TABLE 1-continued

Textural Properties of parent and 10 wt % Fe impregnated over different structured silica.

| Fe/Nanocarrier [wt % g$^{-1}$ support] | BET Surface area [m$^2$/g - support]$^a$ | Pore Surface Area [cm$^3$/g - support]$^b$ | Cumulative Pore Volume (cc/g) [cm$^3$/g - support]$^c$ | Average Pore Diameter [nm]$^d$ |
|---|---|---|---|---|
| MSU-Foam (3D) | 525 | 554 | 2.27 | 40.2 |
| 10 wt % Fe/MSU-Foam | 140 | 134 | 1.30 | 40.2 |
| ULPFDU-12 (3D) | 270 | 284 | 0.33 | 4.7 |
| 10 wt % Fe/ULPFDU-12 | 9 | 7 | 0.02 | 13.1 |
| Si-KIT-6 (3D) | 878 | 862 | 1.23 | 5.7 |
| 10 wt % Fe/Si-KIT-6 | 676 | 616 | 0.96 | 5.6 |

$^a$BET surface area,
$^b$Pore surface area,
$^c$pore volume and
$^d$average pore diameter measured using BJH isotherm.

In case of Q-10 silica, after impregnation, nonsignificant changes were observed with respect to both specific (258 m$^2$/g) and cumulative surface area (274 m$^2$/g), while appreciable pore filling of about 16% (1.22 to 1.02 cm3/g) along with pore diameter decreases from 18.6 to 15.8 nm was observed (Table 1).

Similarly, the surface area of Fe$_2$O$_3$/Si-MCM-41 slightly increased from 923 m$^2$/g to 951 m$^2$/g, while an 11.2% decrease in cumulative surface area, and a 19.3% decrease in the pore volume was observed. The pore diameter only slightly varied from 3.1 to 3 nm after Fe$_2$O$_3$ deposition.

In case of Fe$_2$O$_3$/Q10, surface area deposition remains negligibly small, whereas significant pore volume and pore diameter variations occur. In the case of Fe$_2$O$_3$/Si-MCM-41, cumulative surface area and pore volume decreases, while pore diameter remained unaffected. This shows Fe impregnation over Q10 fills the pore volume and eventually affects pore diameter. In the case of 3D cubic SBA-16, a significant decrease in the textural characteristics was observed. Specifically, a decrease of specific surface area from 980 m$^2$/g to 327 m$^2$/g, and cumulative surface area from 591 m$^2$/g to 194 m$^2$/g, which is about 67% of Fe occupation was observed after Fe impregnation. The cumulative pore volume showed a similar decrease (32%) compared to parent SiSBA-16. Reversely, the average pore diameter increases from 3.3 nm to 4.0 nm. The analysis shows that both surface area and pore volume are being affected and being filled in the 3D pore structure, while enlargement of pore size shows deposition of Fe$_3$O$_4$ around the pore walls that helps to expand the pore size.

In the case of MSU-Foam, reversely a significant change was observed with isotherm and capillary condensation, while pore volume remains mostly unchanged. The pore diameter showed significant variation. The texture of foam type of silica before Fe impregnation was of mesoporous type with high surface area of 554 m$^2$/g, with large pore volume of 2.27 cc/g. The average pore size diameter was of 16 nm before impregnation. The isotherm pattern of mesocellular foam (parent form) and after Fe impregnation are shown in FIGS. 2A and 2B.

Before impregnation, the foam showed characteristic type IV isotherm pattern with H1 hysteresis loop indicating well distributed cells along with windows; P. Schmidt-Winkel, C. J. Glinka, G. D. Stucky, Microemulsion Templates for Mesoporous Silica, Langmuir 16 (2000) 356-361. After impregnation, a significant textural change with respect to surface area and pore volume was observed. A shift in capillary filling P/PO range are observed. Specifically, an occupation of about 73% was observed leading to specific surface area reduction from 525 m$^2$/g to 140 m$^2$/g and about 76% occupation (from 554 m$^2$/g to 134 m$^2$/g) with respect to cumulative surface area was observed. In the case of pore shape retainment, 57.3% of pore filling was observed. The pore diameter of cellular foam increases from 16.4 nm to 40.2 nm. Significantly, the pore diameter showed significant alteration after Fe impregnation. Compared to parent MSU, the pore diameter increases from 16.4 nm to 40.2 nm. Such pattern shows external agglomeration of Fe$_2$O$_3$ particles at the pore surface contributing to expansion in the pore sizes.

The cage type of mesoporous with Fm3m structure (ULPFDU-12) showed typical broad hysteresis indicating interrelated large pores with small sized window type of pores. In this type of material, an abrupt loss in the textural property was observed. With 10 wt % Fe impregnation, about 91% surface occupation was observed, where decrease in surface area occurs from 270 m$^2$/g to 9 m$^2$/g. The pore volume reduced significantly of about 94% from 0.33 ccg$^{-1}$ to 0.02 ccg$^{-1}$. With respect to pore size distribution, similar to cellular foam type, pore size expansion occurred with impregnation from 4.7 ccg$^{-1}$ to 13.1 ccg$^{-1}$.

The cubic structure of Si-KIT-6 with Ia3d symmetry showed 77% of textural filling with 676 m2/g specific surface area and 71% with 616 m2/g cumulative surface area occupation with Fe impregnation. Unlike Si-SBA-16, the pore volume of KIT-6 was sufficient to accommodate the impregnated iron oxide particles. As observed with Si-SBA-16 and MSU Foam type of silicas, the external pore agglomeration was not observed. The impregnation led to the pore volume occupation of 78% that reduces from 1.23 ccg$^{-1}$ to 0.96 ccg$^{-1}$. In addition, KIT-6 pore diameter only marginally reduces from 5.7 to 5.6 nm.

These data show that Si-MCM-41 provided more pore filling, followed by cubic type Si-SBA-16, while Q-10 and MSU-Foam type showed external deposition of Fe$_2$O$_3$ particles, while pore volume remains largely unfilled.

The average size measurement of SPIONs with standard deviation for each sample was calculated (Table 1-2). The average size of the first set of particles was in the range of 3-21 nm and the second of 13-58 nm. The order of SPIONs particle size was found to be in the following order: Silicalite>Q-10>Si-SBA-16>MSU-Foam>Si-MCM-41. Specifically, average SPIONs particle size of the Fe/Si-SBA-16 measured from TEM images was found to be 21.0±1.1 and 9.0±0.3. In support Si-MCM-41, finely dispersed SPIONs in the range of 3-13 nm was observed. Among the support, silicalite showed larger particles in the range of 21-58 nm followed by Q10 silica, which showed of 10-25 nm (FIG. 6).

TABLE 1-2

SPIONs Average particle size estimation (ten or more than ten particles are considered for average size estimation).

| Sample Code | Nanocarriers | Large SPIONs particle size (nm) | Small SPIONs particle size (nm) |
|---|---|---|---|
| ND-53 | Fe/SiSBA-16 | 21.0 ± 1.1 | 9.0 ± 0.3 |
| ND-48 | FeSiMCM-41 | 13.0 ± 1.1 | 3.0 ± 0.2 |
| ND-49 | Fe/Q-10 | 25.0 ± 1.1 | 10.0 ± 0.3 |
| ND-51 | Fe/MSU | 18.0 ± 1.0 | 7.0 ± 0.3 |
| ND-47 | Fe/Silicate | 58.0 ± 5.5 | 21.0 ± 1.5 |

FIG. 3 shows the magnetic property of 10 wt % SPIONs loaded over the different nanocarriers: Q-10, Si-MCM-41, Si-SBA-16, mesocellular foam and Si-KIT-6 Fe/Q-10, respectively (top-to-bottom). Among the different nanocarriers, a magnetically active support order was determined as Fe/Q-10<Fe/SBA-16<Fe/MSU-Foam<Fe/Si-MCM-41<Fe/SiKIT-6. These data showed that Q-10 followed by Si-SBA-16 and MSU-Foam was active, while SiMCM-41 and silicalite was not active.

In case of Fe/Si-KIT-6, though the pore structure was similar to that of Si-SBA-16, did not showed positive magnetization for the dual application of magnetically driven drug delivery approach. The presence of narrow hysteresis loop showed the superparamagnetic behavior of Fe/Q-10, Fe/Si-SBA-16 and Fe/MSU-Foam, respectively. It has been reported that such paramagnetic $Fe^{3+}$ ions are formed through incorporation at the pore walls of support; N. I. Cuello, V. R. Elias, S. N. Mendieta, M. Longhi, M. E. Crivello, M. I. Oliva, G. A. Eimer, Materials Science and Engineering C 78 (2017) 674-681. In case of silicalite, in spite of large iron oxide particles deposition, showed weaker magnetization. These data showed that three samples namely Fe/Q-10, Fe/Si-SBA-16 and Fe/MSU-Foam has the reasonable intrinsic magnetization capability that can be utilized in addition to drug delivery.

FIG. 4 depicts 10 wt % SPIONs loaded over the different nanocarrier (a) Q-10, (b) Si-MCM-41, (c) Si-SBA-16, (d) MSU-foam, (e) Si-KIT-6, (f) ULPFDU-12 and (g) Silicalite, respectively; it also shows the Drs-UV spectra for SPIONs loaded on structured silica samples. These data showed that in spite of loading similar amount of SPIONs, the coordinative dispersion of nanoparticle varies depending on the structural integrity of silicas such as spherical Q-10, hexagonal Si-MCM-41, cubic type of pores of Si-SBA-16, Si-KIT-6, ULPFDU-12, MSU Foam and silicalite. The presence of three types of bands with varying degree of intensity at about 250 nm, 370 nm and 500 nm was observed for analyzed samples. The characteristic absorption band between 200-300 nm shows the dispersed $Fe^{3+}$ cation in tetrahedral coordination due to dπ-pπ charge transfer (Fe-0). The band appearance between 300-450 nm shows the formation of small oligomeric nanocluster, while $Fe_3O_4$ larger clusters are indicated through the presence of broad band between 450-600 nm; Y. Wang, Q. Zhang, T. Shishido, K. Takehira, J. Catal. 209 (2002) 186-196.

In the case of Q-10 silica sample, in addition to tetrahedral coordination, a broad peak appears and extends up to 600 nm; FIG. 4, line (a). Particularly, an intense peak absorption band are observed at about 520 nm that shows formation of large nanoclusters. Therefore, large microspheres silica of Q-10 silica have been shown to assist formation of octahedral species due to extra-framework iron oxide species than isolated tetrahedral iron oxide species. The formation of such octahedral coordinated species are reported to occur due to nanoclusters; N. Cuello, V. Elias, S. Urreta, M. Oliva, G. Eimer, Microstructure and magnetic properties of iron modified mesoporous silica obtained by one step direct synthesis, Materials Research Bulletin 48 (2013) 3559-3563.

In the case of hexagonal pore channels Si-MCM-41 containing SPIONs, the presence of intense tetrahedral species at about 280 nm shows that fine dispersion of iron oxides incorporated in to the framework through Si—O—Fe linkage, see FIG. 4 (b); Y. Lu, J. Zheng, J. Liu, J. Mu, Microporous Mesoporous Mater. 106 (2007) 28-34. The formation of small nanoclusters to smaller extent was also observed with less intense absorption band at 460 nm. Overall, SPIONs/Si-MCM-41 shows formation of finely dispersed SPIONs nanoparticles. Such decreased absorption at longer wavelength shows the systematic deposition and stabilization of $Fe_2O_3$ inside the mesopores leading to reduced mobility of such nanospecies after calcination; N. Cuello, V. Elias, S. Urreta, M. Oliva, G. Eimer, *Microstructure and magnetic properties of iron modified mesoporous silica obtained by one step direct synthesis*, Materials Research Bulletin 48 (2013) 3559-3563.

In case of SPIONs/SiSBA-16, in addition to tetrahedral species a significant proportional of extra framework species occurs at about 530 nm FIG. 4 (c). The less intense tetrahedral absorption band between 200-300 nm shows that distribution of particles is not fine compared to that of Si-MCM-41 support but rather agglomerated type similar to that of Q-10 silica. In particular, the main reason for such agglomeration over cubic Im3m pores of SBA-16 could be attributed to restricted pore entrance size that are relatively smaller than primary mesopore thus limiting the intraparticle mass transfer.

SPIONs/mesocellular foam showed three types of absorption bands, FIG. 4 (d). The foam like pore structure of mesocellular silica induced an absorption peak at 250 nm indicating the presence of tetrahedral Fe species. Comparatively, an intense absorption peak at 370 nm for foam silica showed the presence of small nanoclusters to larger extent, while visible absorption peak at 520 nm shows existence of some large nanoclusters.

Overall the presence of small sized agglomerated octahedral species was found to be higher than Si-MCM-41, while large type of nanoclusters are lesser than that found in SBA-16 cage type of pores and spherical silica. SPIONs/SiKIT-6 with cubic Ia3d pores showed a prominent isolated tetrahedral and small nanoclusters, FIG. 4 (e), compared to cage type of Im3m structure, which showed external agglomerated octahedral species. The large pore volume (1.23 cc/g) of Ia3d cage type of pores of Si-KIT-6 showed the difference with respect to pore filling ability compared to Si-SBA-16 counterpart with Im3m structure (0.49 cc/g) (Table 1).

In addition, the presence of large pore size distributions of Si-KIT-6 showed a non-significant change in pore diameter from 5.7 nm to 5.6 nm, while Si-SBA-16 showed an increase in pore size from 3.3 nm to 4.0 nm indicating pore expanding due to $Fe_2O_3$ deposition around the thick pore walls of Si-SBA-16.

In case of SPIONs/ULPFDU-12, the presence of broad peaks shows characteristics of variable $Fe_2O_3$ deposition occurs at the external surface area; FIG. 4(f). However, structural irregularity with respect to specific surface area, and pore volume (Table 1) shows the deteriorating impact of $Fe_2O_3$ impregnation inside the mesopores leading to disintegration of overall structural parameters (Table 1). The SPIONs over Silicalite (MFI structure) showed no strong absorption bands corresponding to tetrahedral or octahedral coordination; FIG. 4(g).

FIG. 5 shows the FTIR spectra of (a) Q-10 silica, (b) SPIONs/Q-10, (c) Curcumin, (d) Curcumin/Q-10, (e) Curcumin/SPIONs/Q-10, (f) Curcumin/SPIONs/mesocellular foam and (g) Curcumin/SPIONs/SiSBA-16, respectively. Consistent with earlier work (R. Bhandari, et al., Mater. Sci. Eng. C 67 (2016) 59-64), the silica (Q-10) and $Fe_3O_4$ impregnated silica (Q-10) sample did not reveal any significant details; FIG. 5 (a) and (b).

Curcumin spectrum showed the vibration of free hydroxyl groups with distinct peak at 3507 $cm^{-1}$, carbonyl group at 1625 $cm^{-1}$, carbonyl and carbon-carbon double bond at 1603 and 1505 $cm^{-1}$, methylene ($CH_2$) bending vibrations at 1455 $cm^{-1}$, and 1428 $cm^{-1}$, and several peaks corresponding to —C—O—C symmetric and asymmetric vibrations are observed between 1000-1300 $cm^{-1}$; FIG. 5(c).

After curcumin loading over Q-10 silica, additional peaks characteristics of curcumin were observed; FIG. 5. Plot (d).

Bhandari et al. stated that magnetic nanoparticle alone has the capability to hold curcumin through functionalization. Similarly, in the present case, FTIR spectra, FIGS. 5(e) and (g) show that curcumin has been effectively functionalized over SPIONs/silica hybrid composite.

A distinct peak at 962 $cm^{-1}$ corresponding to the enolic hydroxyl group (>C=C(OH)—) was observed for curcumin. After loading curcumin over SPIONs/silica hybrid composite, the peak corresponding to such in-plane bending of OH group of enol decreases considerably indicating functionalization route of curcumin through keto enol functional group. The observed functionalization trend is line with $Fe_3O_4$ nanoparticle for curcumin functionalization. In case of curcumin, the presence of distinct peak at 3504 $cm^{-1}$ shows the hydroxyl functional group. Such band of peak with reduced intensity was also observed for curcumin/SPIONs/structured silica samples.

Compared to curcumin, the peak corresponding to carbon-carbon double bond and carbonyl group at 1603 $cm^{-1}$ reduced significantly indicating interaction of curcumin with SPIONs hybridized silica. It has been shown that the intactness of peak at 1023 $cm^{-1}$ assigned to surface functionalization of C—O—C stretching of $C_6H_5$—O—$CH_3$ group over $Fe_3O_4$ nanoparticle; P. R. K. Mohan, G. Sreelakshmi, C. V. Muraleedharan, R. Joseph, Vib. Spectrosc. 62 (2012) 77-84. These data show that the peak corresponding to $C_6H_5$—O—$CH_3$ group are seen for curcumin at 1025 $cm^{-1}$, but after functionalization, broadening of such peak over SPIONs hybridized Q-10 silica and Si-SBA-16 indicates functionalization at the structured nanopores; FIG. 5, plots (e) and (f).

In case of MSU, the presence of small peak was clearly visible at 1028 $cm^{-1}$, indicating presence of certain proportion of curcumin at the external surface; FIG. 5 (g).

FIGS. 6 and 7 show the SEM micrographs based on comparative surface morphological features of 10 wt % SPIONs loaded over magnetically active nanocarrier: Q-10 silica (FIGS. 6A/7A), SPIONs/Q-10 (FIGS. 6B/7B), SiSBA-16 (FIGS. 6C/7C), SPIONs/SiSBA-16 (FIGS. 6D/7D), mesocellular foam (FIGS. 6E/7E) and SPIONs/mesocellular foam (FIGS. 6F/7F), respectively. The magnification was set to an appropriate value in order to capture the representative features of the specimens in each case.

The Q10 silica shows the presence of spherical shaped microspheres with estimated average size of 100 μm sizes. In case of SPIONs/Q-10, the regularity of the spheres was affected by non-crystalline $Fe_3O_4$ loaded through enforced impregnation technique followed by calcination (FIGS. 6A and 6B). The deposition of nanoclusters was clearly seen at higher scale bar 50 μm compared to parent Q-10 silica (FIGS. 7A and 7B).

A similar irregularly shaped microsphere morphology but with less average sized spheres (~4 μm) was observed in case of SiSBA-16 and SPIONs/SiSBA-16 (FIGS. 6C and 6D).

In case of MSU-Foam, the lower scale bar shows the presence of irregular agglomerated silica forms are observed (FIGS. 7C and 7D). Compared to MSU-Foam (FIGS. 6E and 6F), SPIONs/mesocellular foam clearly shows the porous morphological characteristics changes with agglomerated nanospheres structures at lower scale bar of 3 μm (FIGS. 7E and 7F).

The samples morphology and structure were further analyzed by TEM. FIG. 8 shows the TEM images of 10 wt % SPIONs loaded over different nanocarrier (FIG. 8A) SiSBA-16, (FUG. 8B) Si-MCM-41, (FIG. 8C) Q-10 silica, (FIG. 8D) MSU-Foam and (FIG. 8E) Silicate, respectively.

The TEM analysis shows that SPIONs deposition are unique and depends on the support nature, where the dispersion and agglomeration vary based on the nanocarriers pore architecture. For instance, with three dimensional cage type of SBA-16 pores, the presence of agglomerated forms of SPIONs as nanoclusters were observed along the pore channels (FIG. 8A), while in hexagonal Si-MCM-41 support, the $Fe_2O_3$ particles are finely dispersed (FIG. 8B). The cage type of porous layer of SBA-16 appears to be homogeneous with a fairly constant thickness, and particles were found connected to the layers.

Figure 8F:
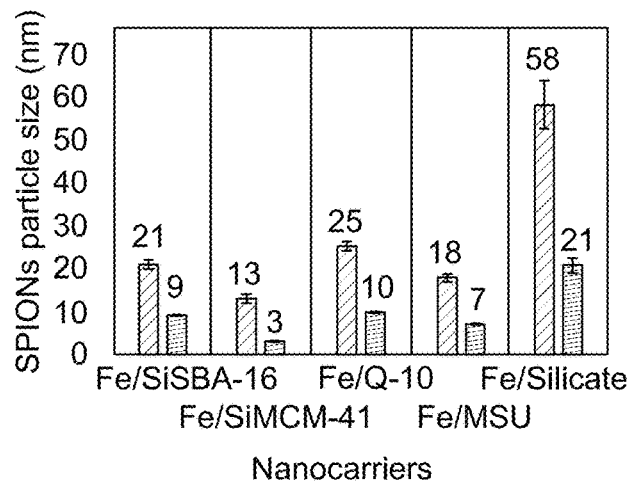

In the case of microsphere Q10 silica, MSU-Foam and silicalite, external agglomeration of SPIONs with varying degree was observed (FIG. 8C-8E). The average size measurement of SPIONs with standard deviation for each sample was calculated. There were two sets of nanoparticles were observed in each case (FIG. 8F). The average size of the first set of particles was in the range of 3-21 nm and the second of 13-58 nm. The order of SPIONs particle size was found to be in the following order: Silicalite>Q-10>Si-SBA-16>MSU-Foam>Si-MCM-41.

Specifically, average SPIONs particle size of the Fe/Si-SBA-16 measured from TEM images was found to be 21.0±1.1 and 9.0±0.3. In support Si-MCM-41, finely dispersed SPIONs in the range of 3-13 nm was observed. Among the support, silicalite showed larger particles in the range of 21-58 nm followed by Q10 silica, which showed of 10-25 nm.

Table 2 shows the adsorption capacity over absence and SPIONs loaded on different nanocarrier supports in solution containing 30 and 60 μg/ml of curcumin in 10% methanol-phosphate buffered saline (pH 7) mixture for 24 h. The adsorption was measured based on the Beer-Lambert's law. The results show that loading of curcumin over SPIONs impregnated structured silica are not affected, rather a slight improvement in the curcumin adsorption was observed compared to parent nanocarriers. Particularly, the percentage adsorption over SiSBA-16 without SPIONs addition was 89.1% and 90.0%, while the adsorption capacity after SPIONs loading improved to 94.1% and 97.3% with 30 and 60 μg/ml solution, respectively In the case of Q-10 silica, Si-MCM-41 and silicalite nanocarrier, an improvement of curcumin adsorption over 30 μg/ml solution was observed.

TABLE 2

Adsorption of curcumin over different structured nanocarriers in absence and presence of SPIONs in solution corntaining 30 and 60 µg/ml of curcumin in 10% methanol-phosphate buffered saline (pH 7) mixture for 24 h

| Nanocarrier | Metal content (wt %) | Role | Initial concentration (µg/ml) | Final concentration (µg/ml) | Adsorption (%) |
|---|---|---|---|---|---|
| Q-10 | — | Single | 30 | 3.18 | 89.4 |
| Fe/Q-10 | 10 | Dual | 30 | 0.64 | 97.8 |
| Q-10 | — | Single | 60 | 1.70 | 97.2 |
| Fe/Q-10 | 10 | Dual | 60 | 1.30 | 97.8 |
| Si-SBA-16 | — | Single | 30 | 3.25 | 89.1 |
| Fe/Si-SBA-16 | 10 | Dual | 30 | 1.76 | 94.1 |
| Si-SBA-16 | — | Single | 60 | 6.00 | 90.0 |
| Fe/Si-SBA-16 | 10 | Dual | 60 | 1.64 | 97.3 |
| Si-MCM-41 | — | Single | 30 | 2.29 | 92.4 |
| Fe/Si-MCM-41 | 10 | Dual | 30 | 1.75 | 94.2 |
| Si-MCM-41 | — | Single | 60 | 2.20 | 96.3 |
| Fe/Si-MCM-41 | 10 | Dual | 60 | 2.18 | 96.4 |
| Silicalite | — | Single | 30 | 6.80 | 78.0 |
| Fe/Silicalite | 10 | Dual | 30 | 3.25 | 89.2 |
| Silicalite | — | Single | 60 | 2.50 | 95.8 |
| Fe/Silicalite | 10 | Dual | 60 | 2.00 | 96.6 |

The percentage adsorption was calculated based on the equation

The percentage adsorption was calculated based on the equation:

Percentage of curcumin adsorption (%)=(Initial curcumin conc−Final curcumin conc)/Initial curcumin conc×100.

The final curcumin concentration was calculated based on the equation=(Final absorbance value× Initial curcumin conc)/Initial absorbance value.

FIG. 9 shows the pictorial representation of curcumin adsorption over a SiSBA-16 nanocarrier and SPIONs/SiSBA-16 at different concentrations ranging from 30-390 µg/ml curcumin/nanocarrier in methanol-phosphate buffered saline (PBS) mixture stirred for 24 h.

The equilibrium adsorption study shows a systematic yellow color variation from light yellow to dark yellow occurs over nanocarrier SiSBA-16 (FIG. 9, samples (a)-(e), while the clear filtrate shows effective adsorption due to large available surface area and accommodatable pore volume (Table 1). In the case of SPIONs/SiSBA-16, similar effective adsorption was observed with increased curcumin loadings. The filtered solution showed no visible brown coloration indicating no apparent diffusion of adsorbed SPIONs nanoparticles from solid to solution phase. Notably, the solid sample coloration after ambient temperature drying showed transformation of color from dark brown to yellow-brown indicating increased curcumin adsorption; FIG. 9, samples (f)-(j).

The curcumin release profile over absence and SPIONs loaded on different nanocarrier supports (powdered form) in PBS solution (pH 5) for 72 hr are shown in FIGS. 10A-10D. These data show that curcumin delivery rate was affected by the pore architecture and SPIONs loading of the structured silica. SPIONs loaded over mesocellular foam showed highest cumulative release than foam itself at fastest rate. The foam composed of largest average pore size (16.4 nm) distribution exhibited highest release that reaches 52.3% for 72 h. The relative ease of curcumin release with respect to foam type mesosilica shows that the interaction might be feeble through hydrogen bonding leading to easy cleavage. It follows that SPIONs loaded SBA-16 with cubic cage narrow pores (3.3 nm) showed lower but slightly enhanced cumulative release compared to parent SiSBA-16. However, the release trend remains stable over the period of 72 h (18.5% for 72 h), which might be due to diffusion through cubic type mesopores. In the case of large type of microspheres Q10 and SPIONs/Q10, showed least curcumin release capability with time (12% in 72 h).

In the case of SPIONs/Si-MCM-41 and SPIONs/Silicalite, compared to parent counterpart, a steady cumulative release trend is observed. The study shows that though impregnation of iron oxides produce very less magnetically active species, it improves the steadiness of the curcumin release behavior. SPIONs/Si-MCM-41 showed cumulative release percentage of 22%, while SPIONs/Silicalite showed 21.1% of curcumin release. Therefore addition of such SPIONs or other types of oxides may facilitate steady release. SPIONs loaded over SiKIT-6 and ULPFDU-12 showed no appreciable difference in the cumulative release trend compared to parent SiKIT-6 and ULPFDU-12. SPIONs/SiKIT-6 and SPIONs/ULPFDU-12 showed release of 21.3% and 11.2%, respectively. However, burst release occurs over such nanoformulations. Huang et al. (2012) reported that such release trend are mainly attributed due to the dispersion of drug at the external surface and drug present at the ultralarge pore entrance of the 3D channels.

In order to fabricate magnetically active drug delivery system, different structured silicas were evaluated by impregnating constant loading of 10 wt % SPIONs. The X-ray diffraction analysis as shown in FIG. 1(a-h) shows that except silicalite, the loaded SPIONs and curcumin were effectively transformed into amorphous form. The textural characterization (FIG. 2 & Table 1) shows that impregnation of SPIONs over different structured silica has unique textural changes and affects the structural integrity of each silica. The spherical Q-10 silica and hexagonal Si-MCM-41 showed very less textural changes with respect to specific and cumulative surface area over Fe impregnation. Both the type of silica showed marginal pore filling.

Contrastingly, the cubic 3D Si-SBA-16 with Im3m symmetry and MSU-Foam showed significant decreases with respect to surface area and as well as pore volume after impregnation. The average pore diameter measurement shows an enlargement after SPIONs impregnation, which signals external deposition of $Fe_2O_3$ particles around the pore walls thereby assisting additional expanded pores. However, in the case of ULPFDU-12, a significant loss in the textural changes (both surface area and pore volume) occurs with $Fe_2O_3$ loadings (Table 1) signaling limited SPIONs loading ability for potential dual applications. The characterization of magnetic property shows that Q-10 microsphere silica showed high magnetic property, followed by SiSBA-16 and mesocellular foam (FIG. 3). The diffuse reflectance study shows that octahedral coordinated species corresponding to small and large nanoclusters are required to induce magnetic property (FIG. 4). A well dispersed SPIONs in hexagonal structure and SPIONs present inside the mesopores of SiKIT-6 are tends to be magnetically non-active (FIG. 3). The FT-IR spectroscopy analysis shows that curcumin functionalization over magnetically active support Q-10 silica and SiSBA-16 occurs majorly inside the structured nanopores, while mesocellular foam indicates presence of certain proportion of curcumin at the external surface (FIG. 5). SEM (FIGS. 6 & 7) and TEM images of SPIONs over different support (FIG. 8) shows the presence of different types of particle size distributions depending on the structural features of nanopores. DRS-UV analysis shows the presence of extra framework species on Q-10, SBA-16 support. While SEM image shows the uniform characteristics between Q-10 and SBA-16, i.e. microspheres. Both supports has unique characteristics built through microspheres though with different particle sizes. The presence of such microspheres might eventually help the $Fe_2O_3$ nanoparticles to be deposited as extra framework species outside the external surfaces and therefore becomes magnetically active. Reversely, in case of Si-MCM-41 and Si-KIT-6, nanocarrier, the presence of nanopores with large pore volume (Table 1) helps the SPIONs to be dispersed well throughout the 1D pore channels (as evidenced from TEM image), leading to magnetically inactive species. The formation of finely dispersed SPIONs nanoparticles are confirmed through TEM analysis (FIG. 8), which showed the nanoparticles are well dispersed in the range of 3-13 nm. In case of Fe/silicalite, extremely large sized Fe particles are agglomerated but are not magnetically active, which shows that such support might form other form of Fe oxide that are not magnetically active. The equilibrium adsorption study shows a systematic color variation of SiSBA-16 from yellow to dark yellow, while brown to yellowish brown are observed over SPIONs/SiSBA-16 (FIG. 9).

The preliminary curcumin release profile shows highest cumulative release with respect to mesocellular foam, while steady drug release found to be for SBA-16. Whereas Q10 silica showed lowest but steady curcumin release (FIG. 10). Comparatively, mesocellular foam shows highest cumulative release within 3 h among the other nanocarriers. The BET surface area analysis shows that increased pore size distribution from 16.4 to 40.2 nm with SPIONs impregnation (FIG. 2 and Table 1). DRS-UV analysis (FIG. 3) and FTIR (FIG. 4) confirms the presence of octahedral $Fe_2O_3$ species and curcumin at the external surface as nanoclusters. Therefore, the addition of curcumin tends to accommodate at the external surface near the pore mouth and that might be the reason for such high cumulative release (Scheme 1). Conversely, in the case of SiSBA-16, the cumulative release is enhanced with SPIONs addition. The textural characterization shows that gradual surface area and pore filling occurs over cubic cage pores without any abrupt pore size variations (FIG. 2 and Table 1). The DRS-UV and TEM analysis (FIG. 4 and FIG. 8) confirms the presence of octahedral species at the external surface as nanoclusters. However, sustained cumulative release trend over SiSBA-16 shows pore diffusional release of curcumin. Such entrapped curcumin may diffuse through the pores slowly leading to sustained release over the tested drug release period of 72 h.

In case of MSU Foam, curcumin deposition tends to occur at the external surface (as evidenced from FT-IR peak of 1028 cm-1) leading to high cumulative release. In the case of hexagonal Si-MCM-41, the presence of high surface area and pore size distribution are able to accommodate SPIONs well as dispersed fine oxides mostly in tetrahedral coordination (FIG. 4), which are supported by TEM analysis that shows visible fine dispersion of oxides in segregated form (3-13 nm) incorporated well into the framework rather than desired agglomeration.

Subsequently, the curcumin drug release also reduced with SPIONs loading that compete with curcumin. In case of silicalite nanocarrier, an enhancement in the release trend was observed over SPIONs/Silicalite (FIG. 10). The cubic cage type of SiKIT-6 (Ia3d symmetry) with the presence of large surface area and pore volume showed different accommodation phenomena. The iron oxides are deposited mostly inside the pore volume of SiKIT-6.

The magnetization analysis showed presence of non-magnetically active species over SiKIT-6 (FIG. 3). In line with Drs-UV spectroscopy, though the cluster formation occurs which are indicated by the octahedral coordinated $Fe_2O_3$ species (FIG. 4), the absence of magnetic active species shows that the deposition might occurs well inside the cubic pores of KIT-6.

This indicates that despite close textural relation with SBA-16, the deposition of $Fe_2O_3$ at the internal or external surface determines the magnetization property, which in turn depends on the unique structural ordering of respective silica.

The pore size distribution of Si-SBA-16 shows the presence of 3D cage type of mesopores in the range of 5 nm (Table 1) in Im3m symmetry.

The generation of pores using pluronic F127 are reported to produce thicker pore walls due to long PO chains of F127, which might help the SPIONs to deposit significant proportional of extra-framework species as nanoclusters.

As shown above nanocarrier textural features are important to tune the iron oxide nanoparticle deposition, which in turn decide the dual response for imaging and therapeutics.

As shown by the Example above, the inventors show that SPIONs loaded on different structured nanocarriers provides a multifunctional magnetic silica based nanocarrier loaded with a deliverable curcumin drug. The magnetic $Fe_3O_4$ was deposited through enforced impregnation methodology on the nanostructured pore surfaces followed by calcination, while curcumin was functionalized through equilibrium adsorption technique. The VSM analysis showed generation of SPIONs over Q-10, SiSBA-16 and mesocellular foam. The magnetically active support was determined as Fe/Q-10>Fe/Si-SBA-16>Fe/MSU-Foam>Fe/Si-MCM-41>Fe/Si-KIT-6. Surface area analysis of magnetically active nanocarriers (Q-10, SiSBA-16 and mesocellular foam) showed that pore filling capability and pore size variation due to external deposition of SPIONs around the pore walls are required to generate magnetically active species. DRS-UV spectroscopy revealed that hexagonal structure favors uniformly distributed $Fe_2O_3$ in nanosizes, while microspheres Q-10 silica, cubic silica SBA-16 (as shown in SEM images), and mesocellular foam showed agglomerated $Fe_2O_3$ crystals as nanoclusters (as evidenced from TEM analysis) and showed super paramagnetic property. ULPFDU-12, KIT-6 and silicalite are found to be magnetically inactive. The absence and presence of SPIONs over different nanocarriers were tested for curcumin release for the period of 3 h. The study showed that higher the magnetization, lesser the cumulative release capacity of curcumin. The curcumin cumulative release ability among magnetically active nanocarriers are as follows MSU-Foam>SiSBA-16>Q-10. In case of magnetically inactive support case, Si-MCM-41 release ability of curcumin reduced but stability of release increased. Silicalite showed improved curcumin release with slight activity reduction over the period of time. In future, the three supports can be further scrutinized for multifunctional capability by engineering nanocarrier through silane functionalization, and enhanced curcumin solubilization technique.

Example 2

Cancer Cell Viability

Materials and Methods/Cell cultures: In this study, a human mammary adenocarcinoma cell line, MCF7, was used for in vitro testing. MCF7 cells were maintained in DMEM (Dulbecco's Modified Eagle Medium) (Gibco, life technologies) supplemented with 10% heat inactivated fetal bovine serum (HI-FBS) (Gibco, life technology), 1% Penicillin Streptomycin (100×-Gibco, life technology), and 1% MEM NEAA (MEM non-essential amino acids) (100×-Gibco, life technology). Cells were kept in a humidified incubator at 37° C. with 5% $CO_2$. For the experimental setup, MCF7 cells were seeded on a 96-well plate at a density of 10,000 cells/well. On the next day, cells were shifted to the starve media (0.5% HI-FBS containing media) for 24 h before treatment.

Treatment: Six groups were tested: Mesocellular foam silica (group I), $Fe_2O_3$ (group II), curcumin (group III), Mesocellular foam silica+$Fe_2O_3$ (group IV), silica+curcumin (group V), and Mesocellular foam silica+$Fe_2O_3$+curcumin (group VI). A stock solution of each condition was freshly prepared for every experiment using 1×PBS (Gibco, life technology) as a vehicle. Subsequently, cells were treated with increasing concentrations of each group as follows: 10, 20, 40, 80, and 100 µg/ml for 24 h.

Cell viability MTT Assay: The viability of cells was tested using 3-(4,5-dimethylthiazol-2-yl)-2,5-diphenyltetrazolium bromide (MTT) assay. It is based on the ability to reduce MTT to formazan crystals. The assay was performed using previously published protocols (Mosmann T. Rapid colorimetric assay for cellular growth and survival: application to proliferation and cytotoxicity assays. J Immunol Methods. 1983 Dec. 16; 65(1-2):55-63. PubMed PMID: 6606682). Briefly, MTT (Sigma-Aldrich) was dissolved in PBS at 5 mg/ml. Working solution of MTT was prepared at a final concentration of 0.5 mg/ml (10 µl of stock MTT+90 µl 1×PBS/well). The 96-well plate was washed twice with 1×PBS and 100 µl of MTT working solution was dispended in all wells. An MTT background control was included, in which MTT working solution was added to empty wells (i.e. no cells). The plate was incubated for three hours at 37° C., followed by the addition of 100 µl of acidified isopropanol solubilizing solution (0.04N HCL isopropanol). The change in color intensity was measured at 570 nm wavelength using SYNERGY-neo2 BioTek ELISA reader. Each condition was performed in triplicates. The reading of each triplicate was averaged and subtracted from the averaged MTT background control reading. Each condition was compared to the control (no treatment) wells. The following equation was used to calculate the % of cell viability:

$$\% \text{ Cell Viability} = \frac{\text{averaged sample read}}{\text{averaged control read}} \times 100$$

Statistics: Cell viability assay data represent five independent experiments. Statistical analysis was performed using Prism 7 software (GraphPad). Analysis was performed using one-way ANOVA with Dunnett's post hoc test.

To investigate the cytotoxic effects of curcumin-loaded/$Fe_2O_3$ impregnated mesocellular foam silica nanoparticles, the inventors assessed cell viability using the MTT assay on MCF7 cells. In that assay, healthy cells will be able to reduce MTT to the purple-colored formazan, while unhealthy/dead cells cannot. MCF7 cells were treated with the following conditions: mesocellular foam silica (group I), $Fe_2O_3$ (group II), curcumin (group III), mesocellular foam silica+$Fe_2O_3$ (group IV), mesocellular foam silica+curcumin (group V), and mesocellular foam silica+$Fe_2O_3$+curcumin (group VI) at increasing concentrations (10, 20, 40, 80, and 100 µg/ml) for 24 h (FIG. 11).

Mesocellular foam silica and $Fe_2O_3$ did not elicit any effect on cell viability either individually (groups I, II) or when combined (group IV). However, curcumin significantly reduced cell viability on its own (group III) and when combined with others (groups V, VI).

Curcumin alone (group III) was able to reduce cell viability to 66.6% and maintain that reduction throughout the different concentrations. Interestingly, when curcumin was combined with either mesocellular foam silica or mesocellular foam silica and $Fe_2O_3$ (groups V, VI), it had a dose dependent reduction in viability that reached to 48.9% (at 100 µg/ml) and 55.4% (at 50 µg/ml), respectively.

It is worth mentioning that when preparing curcumin stock solutions, 390 µg/ml was used for groups III, while only 6.12 µg/ml of curcumin adsorbed on the mesosilica nanoparticles was used for V and VI. This might explain why groups V and VI had a gradual reduction in viability, while group III did not. It also emphasizes the higher efficiency of curcumin when encapsulated in these mesosilica nanoparticles. These results show that the $Fe_2O_3$-coated silica nanoparticles that are loaded with curcumin can effectively reduce viability of the human breast cancer cell line, MCF7 and the therapeutic and drug-delivery advantages of the invention.

As shown in FIG. 11, $Fe_2O_3$ impregnated silica nanoparticles loaded with curcumin significantly reduced cell viability. Percentage of cell viability with the following treatments: mesocellular foam silica, $Fe_2O_3$, curcumin, mesocellular foam silica+$Fe_2O_3$, mesocellular foam silica+curcumin, and mesocellular foam silica+$Fe_2O_3$+curcumin. Treatment concentrations were: 10, 20, 40, 80, and 100 µg/ml for 24 h (n=5 independent experiments). The dashed line represents control which was set as 100% cell viability. Error bars, ±SEM. *P<0.05; **P<0.01 versus control.

Using the MTT cell viability assay, these results show that curcumin indeed reduced cell viability. While 390 µg/ml of curcumin was used to be adsorbed over mesosilica, the equilibrium adsorption showed the presence of 6.12 µg/ml in SPIONs/meso mesocellular foam silica nanoformulation. These in vitro experiments compared curcumin alone (group III-390 µg/ml) to the equilibrium-adsorbed curcumin/SPIONS/mesocellular foam nanoformulation (groups V and VI-6.12 µg/ml). The study showed that curcumin/SPIONs/mesocellular foam silica composite with very low concentration of 6.12 µg/ml was very effective to exert a cytotoxic effect on the breast cancer cell line MCF7. It is about 65 times lower than the required concentration for curcumin alone. This shows the high bioavailability of nanoformulation.

Terminology. Terminology used herein is for the purpose of describing particular embodiments only and is not intended to be limiting of the invention.

The headings (such as "Background" and "Summary") and sub-headings used herein are intended only for general organization of topics within the present invention, and are not intended to limit the disclosure of the present invention or any aspect thereof. In particular, subject matter disclosed in the "Background" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

As used herein, the singular forms "a", "an" and "the" are intended to include the plural forms as well, unless the context clearly indicates otherwise.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

As used herein, the term "and/or" includes any and all combinations of one or more of the associated listed items and may be abbreviated as "/".

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all sub-ranges subsumed therein.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it also describes subranges for Parameter X including 1-9, 1-8, 1-7, 2-9, 2-8, 2-7, 3-9, 3-8, 3-7, 2-8, 3-7, 4-6, or 7-10, 8-10 or 9-10 as mere examples. A range encompasses its endpoints as well as values inside of an endpoint, for example, the range 0-5 includes 0, >0, 1, 2, 3, 4, <5 and 5.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology. As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present invention that do not contain those elements or features.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

The invention claimed is:
1. A method for making a silica nanocarrier comprising superparamagnetic iron oxide nanoparticles (SPIONs) and curcumin, comprising:
   impregnating nanostructured pore surfaces of a platform of nanoporous structured silica with SPIONs to form an impregnated platform of structured silica,
   calcining the impregnated platform of structured silica between 500 and 900° C. to form a calcined platform of structured silica, and adsorbing a curcuminoid onto the calcined platform of structure silica and magnetic nanoparticles to form the silica nanocarrier, wherein the silica nanocarrier comprises a platform of nanoporous structured silica selected from the group consisting of SiSBA-16, Q-10 silica, mesocellular foam, silicalite, mesosilicalite, SiKIT-6, ULPFDU-12, SiMCM-41, ZSM-5, USY, Mordenite, ZSM-11, ZSM-12, ZSM-22, ZSM-23, mesocarbon, graphene oxide and mixtures thereof, wherein the superparamagnetic iron oxide nanoparticles (SPIONS) are present in an amount ranging from about 5 wt % to about 30 wt % based on total weight of the silica nanocarrier, and wherein the curcuminoid is adsorbed on the surface of the nanoporous structured silica.

2. The method of claim 1, wherein the platform of nanoporous structured silica comprises MSU-foam.

3. The method of claim 1, wherein the platform of nanoporous structured silica comprises SiSBA-16.

4. The method of claim 1, wherein the platform of nanoporous structured silica comprises Q-10.

5. The method of claim 1, wherein the SPIONs comprise $Fe_2O_3$ or a mixture of $NiFe_2O_4$, $CuFe_2O_4$, $MnFe_2O_4$ or $CoFe_2O_4$.

6. The method of claim 1, wherein the SPIONs comprise $\gamma$-$Fe_2O_3$.

7. The method of claim 1, wherein the SPIONs have an average particle size ranging from about 7 to about 18 nm when the platform of nanoporous structured silica is MSU-foam, about 9 to 21 nm when the platform of nanoporous structured silica is SiSBA-16; or about 10 to about 25 nm when the platform of nanoporous structured silica is Q-10.

8. The method of claim 1, wherein the curcuminoid is present in an amount ranging from 50 to 70 wt %.

9. The method of claim 1, wherein the silica nanocarrier further comprises a polymer, wherein the SPIONs and/or the curcuminoid is covered with or incorporated into the polymer; and/or wherein one or more components of the composition is functionalized with chitosan, polyacrylic acid, PLGA, or another agent to increase its biocompatibility in vivo.

10. The method of claim 1, wherein the silica nanocarrier further comprises at least one antibody or other targeting agent that binds to cancer cells, neoplasm cells, or tumor cells.

11. The method of claim 1, wherein the silica nanocarrier has a degree of magnetization (M, emu/g) as measured by vibrating sample magnetometry (VSM) greater than an otherwise identical composition wherein the platform of nanoporous structured silica consists of SiSBA-16, Q-10 silica, mesocellular foam, silicalite, mesosilicalite, SiKIT-6, ULPFDU-12 or SiMCM-41.

12. The method of claim 1, wherein the silica nanocarrier has a percentage of cumulative curcuminoid release, in phosphate buffered saline (PBS) at pH 5.6 and 37° C. over 72 hours, greater than an otherwise identical composition wherein the platform of nanoporous structured silica consists of SiSBA-16, Q-10 silica, mesocellular foam, silicalite, mesosilicalite, SiKIT-6, ULPFDU-12 or SIMCM-41.

13. The method of claim 1, wherein the platform of nanoporous structured silica is at least one of MSU-foam SiSBA-16, or Q-10; and the curcuminoid is curcumin which is adsorbed through an equilibrium or enforced adsorption technique.

* * * * *